United States Patent
Baek et al.

(10) Patent No.: US 9,834,752 B2
(45) Date of Patent: Dec. 5, 2017

(54) METHOD FOR IN VITRO EXPANSION OF ERYTHROID CELLS

(71) Applicant: Industry-University Cooperation Foundation Hanyang University, Seoul (KR)

(72) Inventors: Eun-Jung Baek, Gyeonggi-do (KR); Hye-Sook Choi, Gyeonggi-do (KR)

(73) Assignee: INDUSTRY-UNIVERSITY COOPERATION FOUNDATION HANYANG UNIVERSITY, Seoul (KR)

(*) Notice: Subject to any disclaimer, the term of this patent is extended or adjusted under 35 U.S.C. 154(b) by 310 days.

(21) Appl. No.: 14/381,810

(22) PCT Filed: Feb. 28, 2013

(86) PCT No.: PCT/KR2013/001650
§ 371 (c)(1),
(2) Date: Aug. 28, 2014

(87) PCT Pub. No.: WO2013/147425
PCT Pub. Date: Oct. 3, 2013

(65) Prior Publication Data
US 2015/0152386 A1 Jun. 4, 2015

(30) Foreign Application Priority Data
Mar. 30, 2012 (KR) .................... 10-2012-0033361

(51) Int. Cl.
*C12N 5/078* (2010.01)
*C07K 14/435* (2006.01)
*G01N 33/50* (2006.01)

(52) U.S. Cl.
CPC .......... *C12N 5/0641* (2013.01); *C07K 14/435* (2013.01); *G01N 33/5094* (2013.01); *C12N 2501/125* (2013.01); *C12N 2501/14* (2013.01); *C12N 2501/2303* (2013.01); *C12N 2501/39* (2013.01); *C12N 2506/11* (2013.01); *C12N 2513/00* (2013.01); *G01N 2333/47* (2013.01); *G01N 2333/4728* (2013.01)

(58) Field of Classification Search
CPC .............. C12N 5/0641; C12N 2506/11; C12N 2513/00; G01N 33/5094; C07K 14/435
See application file for complete search history.

(56) References Cited

U.S. PATENT DOCUMENTS

2004/0229356 A1* 11/2004 Migliaccio ........... C12N 5/0641
435/372
2008/0300207 A1* 12/2008 Kaufmann ......... C07K 14/4702
514/44 A

OTHER PUBLICATIONS

Lee, G., et al., "Targeted gene deletion demonstrates that the ell adhesion molecule ICAM-4 is critical for erythroblastic island formation," Blood, Sep. 15, 2006, vol. 108, No. 6, pp. 2064-2071.
Zennadi, R., et al., "Epinephrine acts through erythroid signaling pathways to activate sickle cell adhesion to endothelium via LW-αvβ3 interactions," Blood, Dec. 1, 2004, vol. 104, No. 12, pp. 3774-3781.
Kumar, A., et al., "Phorbol Ester Stimulation Increases Sickle Erythrocyte Adherence to Endothelium: A Novel Pathway Involving α4β1 Integrin Receptors on Sickle Reticulocytes and Fibronectin," Blood, Dec. 1, 1996, vol. 88, No. 11, pp. 4348-4358.
Choi, H.S., et al., "Autonomous Control of Terminal Erythropoiesis via Physical Interactions among Erythroid Cells;" Stem Cell Research, 2013, vol. 10, pp. 442-453.

* cited by examiner

*Primary Examiner* — Daniel C Gamett
(74) *Attorney, Agent, or Firm* — Oblon, McClelland, Maier & Neustadt, L.L.P.

(57) ABSTRACT

The present invention relates to a method for in vitro expansion of mature erythroid cells. More specifically, the present invention relates to a method for obtaining concentrated erythrocytes by culturing erythroid cells at high density so as to allow the cells to physically and directly come in contact with each other. Particularly, the method of the present invention is very useful in that it is possible to obtain a large amount of clinically useful concentrated erythrocytes through a small container such as a test tube-sized bioreactor.

11 Claims, 11 Drawing Sheets

METHOD FOR IN VITRO EXPANSION OF ERYTHROID CELLS

CROSS-REFERENCE TO RELATED APPLICATIONS

This application is a §371 national stage entry of International Application No. PCT/KR2013/001650, filed Feb. 28, 2013, which claims priority to South Korean Patent Application No. 10-2012-0033361 filed Mar. 30, 2012, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Dec. 16, 2014, is named G1035-02701_SL.txt and is 20,049 bytes in size.

TECHNICAL FIELD

The present invention relates to a method for in vitro expansion of erythroid cells. More specifically, the present invention relates to a method for producing concentrated erythrocytes by culturing erythroid cells at a high density such that the cells come into direct physical contact with each other. Particularly, according to this method, intercellular signal exchange is activated by the expression of adhesion-related genes DLC-1. ICAM-4, and VLA-4, achieving increased red blood cell (RBC) production.

BACKGROUND ART

Recent advances in science and technology have led to a rapid aging of the population and an increased demand for medical services. Under such circumstances, the use of a larger amount of erythrocytes for transfusion has been required, causing a severe supply shortage of transfusable erythrocytes. Blood transfusion increases the risk of transfusion transmitted infections, which cause serious problems in the use of erythrocytes. Such transfusion transmitted infections include viral contamination caused by various viruses such as human immunodeficiency virus (HIV) and hepatitis type B virus, and bacterial contamination. Newly emerging pathogens responsible for many infectious diseases transmitted by blood transfusion, such as blood-borne tropical diseases and variant Creutzfeldt-Jacob disease, are attributed to an increase in overseas travel and have become serious problems.

Thus, there is a growing need for artificially produced erythrocytes (Greenwalt, T. J.; Zehner Sostok, C.; Dumaswala, U. J. Studies in red blood cell preservation. 1. Effect of the other formed elements. Vox Sang. 58:85-89; 1990; Olsson, M. L.; Clausen, H. Modifying the red cell surface: towards an ABO-universal blood supply. Br. J. Haematol. 140:3-12; 2008).

The current worldwide shortage of transfusable blood causes difficulties in the surgery and treatment of patients. In view of this situation, some researchers have made considerable efforts to produce a large amount of erythrocytes using stem cells. However, most of these efforts still remain at laboratory level where only a small amount of cells proliferate in culture wells.

A previously published report (Mountford et al. Prospects for the manufacture of red cells for transfusion. Br J Haematol. 2010, 149, 22-34) states that an important challenge for mass production of red blood cells is to increase the cell concentration. Although best results of current technology are applied to the manufacture of a single pack of red blood cells, a culture area corresponding to two tennis courts is required, as determined by an arithmetic calculation (Timmins et al. Blood cell manufacture: current methods and future challenges. Trends in Biotechnology 2009, 27, 415-422), making it practically difficult to produce red blood cells on a large scale.

Most of the studies to date have focused on the amplification of early stem cells and progenitor cells. However, little research has been conducted on the terminal maturation of cells, which is substantially the most important stage, and little is known about the reasons for and solutions to low enucleation rate and low cell viability.

As a result of research to solve the problems of the prior art and produce clinically useful concentrated erythrocytes even in a small-scale space, the present inventors have found that when erythroid cells are cultured at a high density such that the cells come into direct physical contact with each other or in the presence of ICAM-4 protein, the protein mediates binding between the erythroid cells and the resulting intercellular signal exchange is activated, achieving high productivity of erythrocytes. The present invention has been accomplished based on this finding.

DISCLOSURE

Technical Problem

The present invention has been made in an effort to solve the problems of the prior art, and it is a principal object of the present invention to provide a method for in vitro expansion of erythroid precursor cells by which clinical grade erythrocytes can be produced (expanded or concentrated) on a large scale.

It is a further object of the present invention to provide a marker composition for erythroid cell differentiation.

It is another object of the present invention to provide a method for increasing the terminal maturation of erythroid cells by promoting the expression or activity of DLC-1, ICAM-4 and VLA-4.

TECHNICAL SOLUTION

One aspect of the present invention provides a method for in vitro expansion of erythroid cells, including culturing erythroid cells at a high density such that the cells come into direct physical contact with each other or in the presence of ICAM-4 protein.

The erythroid cells include cells in the stages of maturation from erythroid progenitor cells. Particularly, the erythroid cells are preferably those that almost complete their maturation stages and more preferably include those that exit the terminal maturation stage. At the terminal maturation stage, the erythroid cells undergo enucleation.

The high-density culture refers to culture at a high density to cause intercellular contact from the stage of seeding. When applied to a 2D plate, the high-density culture is performed at at least 100% confluence, for example, at 100-200% confluence, preferably at 100-150% confluence, as calculated from the cell area per plate area. The culture at 100% and 150% confluences include cell seeding and culture at a density of about $5.0 \times 10^6$ cells/2 $cm^2$ (2 $cm^2$ corresponds to the bottom area of a 24-well plate) and a density of about $7.5 \times 10^6$ cells/2 $cm^2$, respectively.

The culture in the presence of ICAM-4 protein may be performed, for example, by the introduction of an ICAM-4 expression vector or the addition of ICAM-4 protein.

The erythroid cells may be cultured, for example, in a 2D configuration using a plate or a 3D configuration using a tube. Preferably, the 3D culture is performed in a state in which the erythroid cells are allowed to settle and packed.

In the present invention, the erythroid cells express adhesion-related genes of DLC-1, ICAM-4, and/or VLA-4 during culture. Intercellular signal exchange is activated by the expression of the adhesion-related genes, resulting in an increase the productivity of red blood cells, like hematopoiesis regulated by the expression of adhesion-related genes in the bone marrow.

Particularly, binding and signal transduction between the erythroid cells during culture are stimulated via ICAM-4 protein to be expressed or the ICAM-4 protein added.

In a further embodiment of the present invention, DLC-1. ICAM-4, and VLA-4 proteins may be further added to the cell culture medium during the erythroid cell culture, resulting in high production efficiency.

Particularly, the present inventors have succeeded for the first time in demonstrating a relationship between DLC-1 and a secretory form of ICAM-4 and the differentiation and maturation of erythroid cells. This demonstration has great significance in that DLC-1, which is only known to be associated with cancer cells, plays a role in the proliferation and differentiation of normal cells. The present inventors also discovered for the first time that a secretory form of ICAM-4 is expressed at the terminal maturation stage in the differentiation of human erythroid cells.

As the maturation of erythroid cells proceeds, the expression levels of DLC-1 and ICAM-4 increase until enucleation. Thus, a further embodiment of the present invention provides a marker composition for erythroid cell differentiation including DLC-1 and/or ICAM-4.

DLC-1 and ICAM-4 may consist of the nucleic acid sequences set forth in SEQ ID NOS: 1 and 2, respectively, but may be appropriately modified so long as their functions are maintained unchanged.

DLC-1 emits adhesion-related signals in association with ICAM-4 and activates the signal exchange among erythroid cells, resulting in an increase in the productivity of red blood cells.

In a similar aspect, another embodiment of the present invention provides a method for increasing the maturation, particularly, the terminal maturation of erythroid cells, the method including promoting the expression or activity of DLC-1, VLA-4 and ICAM-4. The promotion of the expression or activity of DLC-1, VLA-4 and ICAM-4 enables in vitro expansion of erythroid cells to a level such that final erythrocytes are clinically useful.

The terminal maturation of erythroid cells includes enucleation, which is activated by promoting the expression or activity of DLC-1, VLA-4 and ICAM-4. The ICAM-4 gene can be expressed to produce a secretory form or membrane-bound form of protein, preferably a secretory form of protein.

That is, according to the present invention, the expression of DLC-1, VLA-4 and ICAM-4 increases the activity of signal exchange between mature erythroid progenitor cells (polychromatophilic or orthochromatic erythroblasts) and increases the terminal maturation of erythroid cells.

The expression or activity of DLC-1, VLA-4 and ICAM-4 may be promoted by various methods known in the art. For example, DLC-1, VLA-4 and ICAM-4 may be introduced into the erythroid cells.

The methods and composition according to the present invention can be advantageously applied to mass production (expansion, concentration, and amplification) of human erythrocytes in a small-scale system such as a bioreactor system.

Advantageous Effects

According to the method of the present invention, erythroid cells are cultured at a high density such that the cells come into direct physical contact with each other or in the presence of ICAM-4 protein. The method of the present invention increases the expression of adhesion-related genes and the resulting intercellular signal exchange activity, effectively increasing the productivity of erythrocytes even in a small-scale bioreactor system. That is, the method of the present invention enables expansion of erythroid cells to produce clinically useful erythrocytes even in a small space.

Therefore, the present invention is in contradiction to the known report that a culture area corresponding to at least two tennis courts is required to manufacture a single pack of red blood cells and a 1000 L bioreactor is needed for final culture, as determined by optimal theoretical calculation, making it practically difficult to produce erythrocytes on a large scale. The method of the present invention enables the manufacture of one pack of concentrated erythrocytes in a 200-400 mL (0.2-0.4 L) space on a packed state where intercellular contact is maximized.

MODE FOR INVENTION

Figure 1:
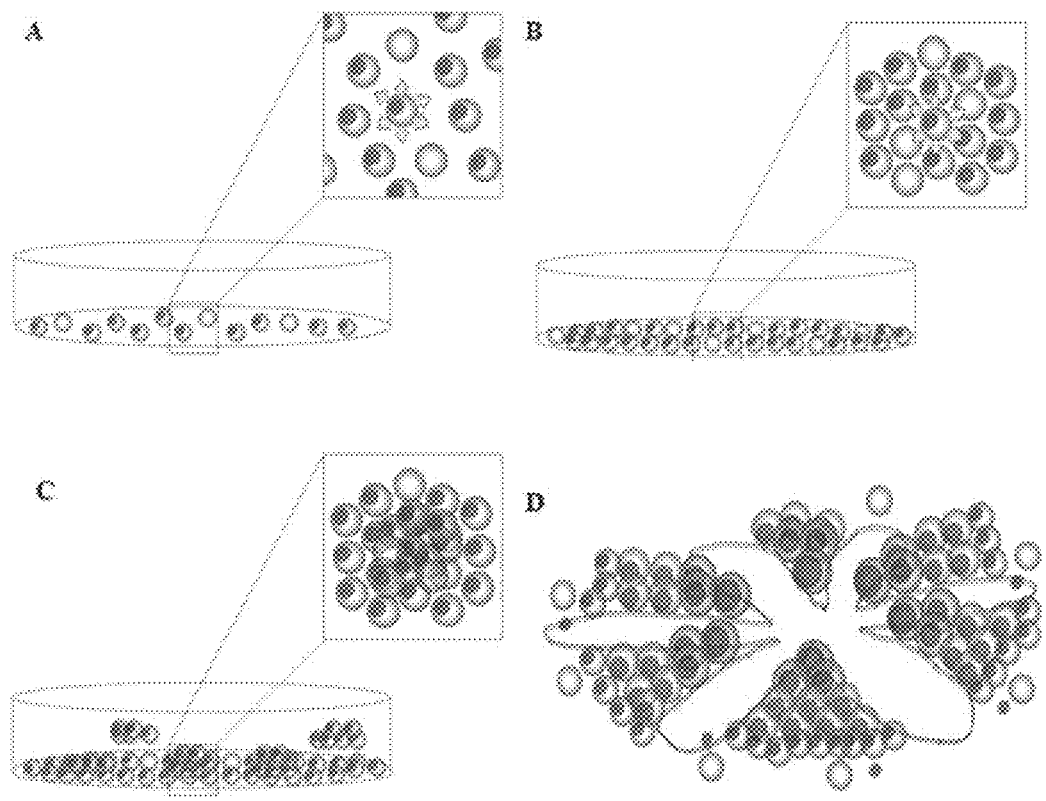
FIG. 1 schematically shows erythroid cell cultures at different densities according to embodiments of the present invention and shows images of the cells cultured at the respective densities.
Figure 1:
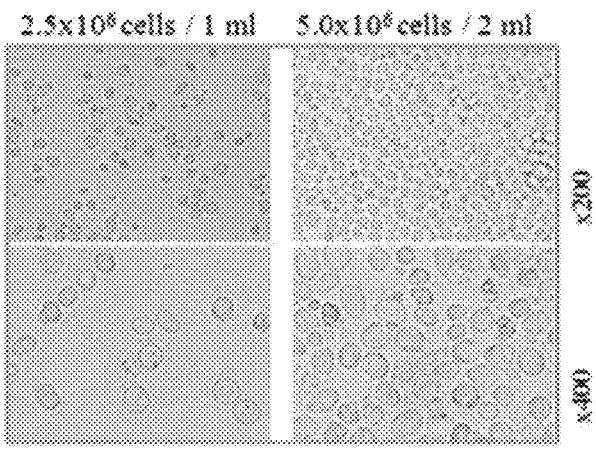

The terms used herein are defined below.

By "nucleic acid" is meant to include any DNA or RNA, for example, chromosomal, mitochondrial, viral and/or bacterial nucleic acid present in tissue sample. The term "nucleic acid" encompasses either or both strands of a double stranded nucleic acid molecule and includes any fragment or portion of an intact nucleic acid molecule.

By "gene" is meant any nucleic acid sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The nucleic acid sequence may contain a genetic abnormality within exons, introns, initiation or termination regions, promoter sequences, other regulatory sequences or unique adjacent regions to the gene.

The term "primer" or "primers" refers to oligonucleotide sequences that hybridize to a complementary RNA or DNA target polynucleotide and serve as the starting points for the stepwise synthesis of a polynucleotide from mononucleotides by the action of a nucleotidyltransferase, as occurs for example in a polymerase chain reaction.

The term "recombinant protein" refers to a protein that is produced through recombinant DNA. The recombinant DNA refers to DNA made by genetic recombination technology in which a gene is introduced into cells through a vector and exhibits its functions in the cells. The recombinant protein is a final product made by genetic recombination technology and indicates the possibility of mass production and processing.

Progenitor cells are undifferentiated cells with self-replication ability and differentiation potency, but for which type of ultimately differentiated cell is predetermined. Progenitor cells differentiate through predetermined pathways but generally do not express a marker of fully differentiated mature cells or do not function as fully differentiated mature cells. Accordingly, progenitor cells differentiate into related cell types but cannot form a wide variety of cell types in normal states. Erythroid progenitor cells are used in the present invention.

The term "differentiation" used herein refers to a phenomenon in which the structure or function of cells is specialized during the division, proliferation and growth thereof, that is, the feature or function of cell or tissue of an organism changes in order to perform work given to the cell or tissue. Generally, it refers to a phenomenon in which a relatively simple system is divided into two or more qualitatively different partial systems. For example, it means that a qualitative difference between the parts of any biological system, which have been identical to each other at the first, occurs, for example, a distinction, such as a head or a body, between egg parts, which have been qualitatively identical to each other at the first in ontogenic development, occurs, or a distinction, such as a muscle cell or a nerve cell, between cells, occurs, or the biological system is divided into qualitatively distinguishable parts or partial systems as a result thereof.

The term "expansion (concentration or amplification)" refers to an increase in the number of cognate cells after division and it usually refers to an increase in the number of cells in a multicellular organism. When cells are proliferated (amplified) to reach a certain level in number, their traits are generally changed (differentiated) and are simultaneously controlled. In many cases, an increased number of cells and neogenesis of cytoplasm in cells are distinguished from cell growth. However, when an increased number of cells are estimated from a biological viewpoint, it is reasonable to regard the time when no differentiation occurs at the developmental stages of a multicellular organism is regarded as proliferation (expansion or amplification). The three terms are used interchangeably herein.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "include (comprise)." "includes (comprises)." and "including (comprising)" will be understood to imply the inclusion of a stated step or element or group of steps or elements but not the exclusion of any other step or element or group of steps or elements.

The present invention will now be described in detail.

The present inventors have earnestly conducted research to develop a method for producing (expanding or concentrating) erythrocytes in vitro on a large scale, and as a result, found that when erythroid cells are cultured at a density at least about 10-fold higher than that known previously for expansion of the erythroid cells such that the cells come into direct physical contact with each other, a single pack of concentrated erythrocytes can be manufactured in vitro in a small-scale system. The present inventors have also found the expression of specific adhesion-related genes DLC-1. ICAM-4, and VLA-4 during the high-density culture, particularly, ICAM-4-mediated binding between erythroid progenitor cells.

Based on these findings, the present inventors have succeeded in developing a method for the mass production of erythrocytes in an efficient manner by erythroid cell culture in the presence of ICAM-4 protein instead of high-density culture.

The present invention is in complete contradiction to the known report that a culture area corresponding to about two tennis courts is required to manufacture a single pack of red blood cells and shows the possibility of producing one unit (U) of concentrated erythrocytes even in an incubator having a cross-sectional area corresponding to 1/260.8 of that reported before or an incubator having a volume of 2 m$^3$, suggesting the production of erythrocytes on an industrial scale.

The present invention is directed to a method for in vitro expansion of erythroid cells.

The erythroid cells include all cells in the stages of maturation from erythroid progenitor cells. Particularly, the erythroid cells are preferably those that almost complete their maturation stages, most preferably polychromatophilic erythroblasts and orthochromatic erythroblasts in the terminal maturation stage. At the terminal maturation stage, the erythroid cells undergo enucleation.

The erythroid progenitor cells can be obtained from various sources, for example, peripheral blood, cord blood and bone marrow. CD34+ cells as the erythroid progenitor cells can be isolated by suitable methods known in the art, for example, an immunomagnetic-bead selection method using CD34+ antibody. According to a preferred embodiment of the present invention, the CD34+ cells may be cells derived from cord blood.

The erythroid progenitor cells differentiate into mature erythrocytes via erythropoiesis consisting of the following stages: (a) differentiation from hematopoietic stem cells to proerythroblasts; (b) differentiation from the proerythroblasts to basophilic erythroblasts; (c) differentiation from the basophilic erythroblasts to polychromatophilic erythroblasts; (d) differentiation from the polychromatophilic erythroblasts to orthochromatic erythroblasts; (e) differentiation from the orthochromatic erythroblasts to polychromatic erythrocytes; and (f) differentiation from the polychromatic erythrocytes to erythrocytes.

Preferably, the erythroid cells used in the present invention include the cells in the maturation stages (d), (e), and (f).

According to the method of the present invention, the cells in the maturation stages can be expanded and/or concentrated to an industrially applicable level so that packs of erythrocytes for clinical use can be manufactured on a large scale.

One specific aspect of the present invention is directed to a method for in vitro expansion of erythroid cells, including culturing erythroid cells at a high density such that the cells come into direct physical contact with each other.

That is, according to the method of the present invention, erythroid cells are cultured at a high density such that they come into direct physical contact and interact with each other.

The high-density culture is not traditional seeding at 30-70% confluence to allow spaces for cell proliferation but means cell culture at high density to cause intercellular contact from the stage of seeding.

There is no restriction on the system for cell culture. In the case of 2D culture, a 2D plate may be used. In this case, the cells are cultured at at least 100% confluence, as calculated from the cell area per plate area. For example, the cells may be cultured at 100-200% confluence, preferably 100-150% confluence. The 100% confluence corresponds to a density at least about 10-fold higher than the conventional cell density for erythroid cell culture. In the case of 3D culture, the cells are cultured in a state in which the cells are allowed to settle and packed in a cell culture space. In this case, about $2 \times 10^{12}$ cells are contained in a 200-400 mL unit of donated blood.

In addition to this physical contact, it is required to maintain the cell concentration per culture medium constant. 1, 2, and 3 mL of culture media are preferably added for the culture conditions of 50, 100, and 150% confluences, respectively, to maintain the concentration of nutrients or cell metabolic waste at a constant level.

The erythroid cells may be cultured, for example, in a 2D configuration using a plate or a 3D configuration using a tube. Preferably, the 3D culture is performed in a state in which the erythroid cells are allowed to settle and packed. In the examples section that follows, the cells cultured on a packed state were confirmed to have much higher viability. This result reveals that the culture method based on 3D contact is applicable to mass RBC production because its ability to maximize contact between the erythroid cells.

In one embodiment of the present invention, the high-density culture allows for physical direct contact between the erythroid cells, resulting in interactions between the erythroid cells. In the Examples section that follows, the direct contact between the erythroid cells was confirmed by fluorescence microscopy observation after staining of the cell membranes and the interactions between the cells were demonstrated. The erythroid cells cultured in a state in which the cells are allowed to settle and packed were confirmed to have high cell viability.

In the method of the present invention, the erythroid cells in physical direct contact with each other express adhesion-related genes such as DLC-1, ICAM-4, and VLA-4 during culture.

As the erythroid cell density increases in accordance with the method of the present invention, the expression of the adhesion-related genes DLC-1, ICAM-4 and VLA-4 increases and the resulting intercellular signal exchange is activated. This activated intercellular signal exchange increases the yield of red blood cells. Particularly, binding between the erythroid cells is mediated by ICAM-4, which binds to DLC-1 to form bonds between the erythroid cells.

Based on the above mechanism, a further specific aspect of the present invention is directed to a method for in vitro expansion of erythroid cells, including culturing erythroid cells in the presence of ICAM-4 protein.

The method of the present invention is on the basis of the finding that binding between erythroid cells is mediated by ICAM-4 and is featured in that erythroid cells are cultured in the presence of ICAM-4 protein. The culture in the presence of ICAM-4 protein is performed by the introduction of an ICAM-4 expression vector. For the purpose of introducing the ICAM-4 expression vector, gene delivery systems and gene manipulation techniques known in the art may be appropriately used by those skilled in the art.

The erythroid cell culture in the presence of ICAM-4 at the initial stage has the same effects as the high-density culture even without direct intercellular binding. In proportion to the cell concentration at the stages of maturation, the viability of erythroid cells increases and the nuclear division of erythroid cells is hindered to decrease the incidence of dysplasia that blocks erythropoiesis. As a result, the enucleation rate of erythroid cells increases, eventually bringing about an increase in the yield of final erythrocytes.

According to the methods for in vitro expansion of erythroid cells, erythroid cells are cultured at a high density such that the cells come into direct physical contact with each other or in the presence of ICAM-4 protein, as described above.

The erythroid cells used in the methods of the present invention express adhesion-related genes such as DLC-1, ICAM-4, and VLA-4, the functions of which are to activate intercellular signal exchange to increase the productivity of red blood cells.

Based on this mechanism, a further embodiment of the present invention provides a method for in vitro expansion of erythroid cells, including adding DLC-1. ICAM-4, and VLA-4 proteins to a culture medium of erythroid cells during culture to create an environment similar to that of the high-density culture.

The proteins may also be added by a 2D or 3D culture method, which has been explained above. Particularly, when erythroid cells are cultured using a suitable system such as a bioreactor, this protein addition can be easily used as means to further increase the production efficiency of erythrocytes.

In another aspect, the present invention is directed to functions of the genes DLC-1, ICAM-4, and VLA-4 that are expressed during erythroid cell culture.

Particularly, VLA-4 is a gene essential for in vivo and in vitro differentiation and expansion of erythroblasts and is known to be highly expressed during erythropoiesis (Dormer et al.). However, the expression of DLC-1 in erythroid cells has not previously been reported.

The present inventors identified for the first time the expression of DLC-1 in K562 cells, a human erythroid cell line, that can induce differentiation into erythrocytes. Particularly, the present inventors found the fact that DLC-1 is involved in the differentiation process, particularly the maturation process of erythroid cells.

The expression of DLC-1 further increases during enucleation and binds to VLA-4 to emit adhesion-related signals, thereby further activating the enucleation and the final maturation stage. Therefore, as erythroid cells undergo differentiation-specific stages. i.e. maturation stages, the expression of DLC-1 increases. As a result, DLC-1 may function as a marker for erythroid cell differentiation (maturation).

The present inventors identified for the first time the expression of a secretory form of ICAM-4 in human erythroid cells. The expression of the secretory form of ICAM-4 affects the activity of intercellular signal exchange.

Thus, another aspect of the present invention is directed to a marker composition for erythroid cell differentiation including DLC-1 and/or ICAM-4. For example, the composition may be used to determine whether erythroid cells are in the terminal maturation stage. The marker composition of the present invention may include DLC-1 as a major ingredient, preferably two genes DLC-1 and ICAM-4 as major ingredients.

In a further aspect, the present invention is directed to a method for increasing the terminal maturation of erythroid cells, including promoting the expression or activity of DLC-1. As explained earlier, the terminal maturation of erythroid cells includes enucleation.

The promotion of the expression or activity of DLC-1 may be achieved concurrently with the promotion of the expression or activity of VLA-4 and/or ICAM-4 genes.

The expression or activity of DLC-1, VLA-4, and ICAM-4 may be promoted by the introduction of DLC-1 into erythroid cells. The introduction (transduction) of DLC-1, VLA-4, and ICAM-4 refers to the introduction of nucleic acids encoding the genes into erythroid cells.

The genes may be introduced into erythroid cells by suitable methods known in the art. Examples of such methods include DNA-calcium precipitation and electroporation. Liposomes, polyamines, retroviruses, and adenoviruses may also be used to introduce the genes into erythroid cells. In one embodiment, the method includes inserting nucleic acids encoding DLC-1 into separate expression vectors or a single expression vector and introducing the resulting expression vector(s) into erythroid cells.

The nucleic acids encoding DLC-1, VLA-4, and ICAM-4 are not limited so long as they have base sequences known to encode DLC-1, VLA-4, and ICAM-4 in the art.

The nucleic acids may have base sequences encoding functional equivalents of DLC-1, VLA-4, and ICAM-4. The functional equivalents are polypeptides that have a sequence having a homology of at least 70%, preferably at least 80%, more preferably at least 90% to the amino acid sequences encoded by the nucleic acid sequences set forth in SEQ ID NOS. 1, 2 and 3 as a result of addition, substitution or deletion of amino acids and exhibit substantially the same physiological activity as that of DLC-1. By 'the same physiological activity' is meant activity that emits adhesion-related signals in erythroid cell expansion to further activate the enucleation and final maturation stage of erythroid cells.

The nucleic acids encoding DLC-1, VLA-4, and/or ICAM-4 may be prepared by gene recombination techniques known in the art (Sambrook, Fritsch and Maniatis, 'Molecular Cloning, A laboratory Manual, Cold Spring Harbor laboratory press, 1989; Short Protocols in Molecular Biology, John Wiley and Sons, 1992). Examples of such gene recombination techniques include PCR techniques for amplifying nucleic acids from genome, chemical synthesis techniques, and techniques for cDNA sequence production. According to the method of the present invention, the recombinant DLC-1, VLA-4, and/or ICAM-4 proteins synthesized by these techniques are added to the culture medium.

According to the method of the present invention, the erythroid cells may be proliferated and expanded by a suitable technique or a modification thereof known in the art.

In one embodiment, the culture medium may be a stroma-free, serum-free, and/or plasma-free medium. The culture medium may be a cell culture minimum medium (CCMM) including a carbon source, a nitrogen source, and trace elements only. Examples of such cell culture minimum media include commercially available media such as Dulbecco's modified Eagle's medium (DMEM), endothelial differentiation medium (EDM), minimal essential medium (MEM), basal medium Eagle (BME), RPMI 1640, F-10, F-12, α-minimal essential medium (α-MEM), Glasgow's minimal essential medium (G-MEM), and Iscove's modified Dulbecco's medium, and artificially synthesized media.

The medium may include vitamin C to maintain a stable state from oxidative stress in vitro. The medium may optionally further include an antibiotic such as penicillin, streptomycin or gentamicin. The medium may further include at least one factor selected from stem cell factors, interleukin-1, interleukin-3, interleukin-4, interleukin-5, interleukin-11, granulocyte macrophage colony-stimulating factors, macrophage colony-stimulating factors, granulocyte colony-stimulating factors, and erythropoietin.

In the method of the present invention, the erythroid cells may be cultured in a general incubator (for example, a $CO_2$ incubator) or a bioreactor.

Figure 13:
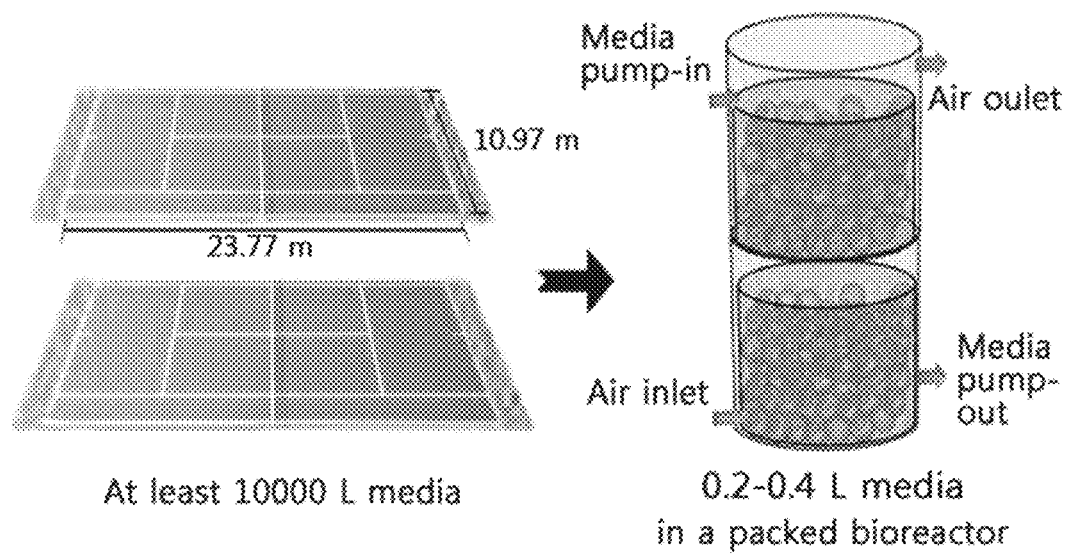
FIG. 13 is a diagram comparing the cell culture areas and volumes required to manufacture one pack of concentrated erythrocytes in a method of the prior art and a method of the present invention.

As described above, according to the method of the present invention, erythroid cells are cultured at a high density such that the cells come into direct physical contact with each other or in the presence of ICAM-4 protein. This cell culture activates intercellular signal exchange to enable the production of erythrocytes at a high concentration. The present invention is in contradiction to the known report that a culture area corresponding to two tennis courts is required to manufacture a single pack of red blood cells, making it practically difficult to produce erythrocytes on a large scale, and demonstrates the production of erythrocytes in a very small bioreactor with a bottom area of 1 $m^2$ and a height of 2 m, suggesting the production of erythrocytes on an industrial scale (FIG. 13).

Specifically, the method of the present invention enables the production of one pack of concentrated erythrocytes in an area corresponding to 1/260.8 of that reported before.

Concentrated erythrocytes produced by the method of the present invention can be used in various therapeutic applications.

In a specific embodiment, erythrocytes produced by the method of the present invention may be used for transfusion. The method of the present invention can alleviate chronic blood shortages, which are problems encountered in blood banks and hospitals in Korea, due to its ability to produce a large amount of cells for transfusion. The method of the present invention allows for the production of universal cells for transfusion.

In a specific aspect, the present invention is directed to the expansion of human erythroid cells to produce red blood cells on a commercial scale.

According to the method of the present invention, human red blood cells are produced on a large scale. The human red blood cells are supplied to hospitals, clinicians, and other health care facilities. In some cases, the human red blood cells may be stored until supply. When a patient suffers from a disease for which medicine is efficacious, such as an ischemic or vascular injury, or requires hematopoietic reconstruction, human red blood cells may be ordered or delivered to the patient in a timely manner. Thus, the present invention is directed to a method for expanding human erythroid cells to produce red blood cells on a commercial scale, a cell preparation including human red blood cells produced by the method, and a method for supplying human red blood cells to hospitals and clinicians (i.e. including producing, optionally storing, and selling human red blood cells).

In a further specific aspect, the present invention is directed to a method for producing, storing, and distributing red blood cells expanded by the foregoing method. According to the method of the present invention, a large quantity of human red blood cells can be produced, harvested, and purified. The human red blood cells may be optionally stored before treatment of patients. Thus, a specific embodiment of the present invention provides a method for supplying red blood cells to hospitals, health care centers, and clinicians. Red blood cells produced by the foregoing method of the present invention are stored, supplied to a hospital, health care center or clinician on demand, and administered to a patient in need of red blood cell therapy.

EXAMPLES

The present invention will be explained in more detail with reference to the following examples. It will be obvious to those skilled in the art that these examples are provided for illustrative purposes only and should not be construed as limiting the scope of the invention.

Example 1: Production and Characterization of Red Blood Cells

1. Cell Culture and Enumeration

CD34+ cells were isolated from the cord blood of healthy donors by using the immunomagnetic microbead selection method and EasySep CD34 isolation kit (StemCell Technologies, Vancouver, Canada).

The CD34+ cells were frozen and stored until use. During frozen storage for 17-18 days, the cells were cultured to a density of $3 \times 10^5$ cells/ml under stroma- and serum-free conditions.

Several cytokines were added to induce the CD34+ cells to differentiate. From day 0 to day 7, the cells were cultured in media supplemented with 10 μm hydrocortisone (Sigma), 100 ng/ml stem cell factor (SCF; R&D Systems, Minneapolis, USA), 10 ng/ml interleukin (IL)-3 (R&D Systems), and 6 IU/ml erythropoietin (EPO; Calbiochem, La Jolla, Calif., USA).

From day 7 to day 13, the expanded erythroblasts were cultured in 50 ng/ml SCF, 10 ng/ml IL-3, and 3 IU/ml EPO. From day 13 to day 17, 50 ng/ml SCF and 2 IU/ml EPO were added. The culture media were replenished every other day. From day 13, the cells were cultured without the addition of cytokines. The cells were cultured in a $CO_2$ incubator (Sanyo, Japan) at 37° C. The cells were counted by trypan blue staining and only live cells were included for cell expansion analysis.

2. Cell Culture for Density Effects

The cells were maintained at a low density from the beginning of culture until day 13. In this stage, the cells were found to expand too rapidly to maintain a constant density. The cells were still active and their viability remained high independent of cell density.

2-1. 2D Culture

On day 17 of culture, orthochromatic erythroblasts were seeded on well culture plates to reach 50% ($2.5 \times 10^6$ cells/ml), 100% ($5.0 \times 10^6$ cells/2 ml), and 150% ($7.5 \times 10^6$ cells/3 ml) confluences (FIG. 1A-C).

The cultures were checked daily to confirm their confluences, which were determined by cells flocking to the centers of the plates. The media were replenished every day and the confluences were regulated to maintain the same culture state. The cell confluences were observed under phase contrast microscopy and Wright-Giemsa staining was used to verify cell integrity, which was defined as whether the cells were damaged.

2-2. 3D Culture

Simultaneously with the 24-well culture (2D culture), erythroid cells were added to and packed in EP tubes to observe whether they could be cultured on a packed state in which contact between the cells was most maximized and whether cell viability decreased or cell aggregation occurred. Thereafter, live cells were counted weekly and cell morphology was observed under phase contrast microscopy.

3. Imaging of Red Blood Cells

Cell morphology was analyzed by cytospinning using a cell centrifuge (Cellspin, Hanil Science Industrial, Seoul, Korea) and subsequent Wright-Giemsa staining (Sigma-Aldrich).

400-450 cells for each density and time point were counted to measure enucleation rates. The stained cells were imaged using a digital camera (Eclipse TE2000-U, Nikon, Japan) and the Nikon ACT-1 program.

4. Determination of Cell Viability

Cell viability was determined using trypan blue staining and flow cytometry analysis using Annexin V. The cells were stained with Annexin V-PE and propidium iodide (BD PharMingen, Franklin Lakes, N.J.) at room temperature for 15 min. The stained cells were washed twice with cell buffer and analyzed by flow cytometry.

5. Flow Cytometry for Red Blood Cell Detection

Red blood cells were labeled with anti-human antibodies (i) glycophorin A (GPA)-FITC (BD PharMingen, Franklin Lakes, N.J.) and (ii) CD71-FITC (eBioscience, San Diego, Calif.) on days 13, 17, and 21 to measure changes in phenotype during growth of the cells. Immunoglobulin G1 (IgG1)-FITC and IgG1-PE (Beckman Coulter, Miami, Fla.) were used as isotype controls. For immunophenotype determination, the cells were washed with phosphate buffered saline (PBS) and incubated with respective monoclonal antibodies at 4° C. for 15 min. After washing, the cells were suspended in phosphate buffered saline (PBS) and analyzed using flow cytometry.

FITC-conjugated anti-HbF (fetal Hb) and PerCP-conjugated anti-Hbβ (adult Hb) (BD PharMingen) were used to measure the intracellular expression of hemoglobin (Hb). Briefly, the cells were re-suspended in cold 0.05% glutaraldehyde at room temperature for 10 min, washed with phosphate buffered saline (PBS) containing 0.1% bovine serum albumin, and suspended in 0.1% triton X-100 at room temperature 5 min. After washing, antibodies were added to the cells at room temperature for 15 min, followed by washing. The stained cells were analyzed using a flow cytometer (BD FACSCalibur™ (BD Biosciences, San Jose, Calif.) provided with software.

6. Fluorescence Staining and Cell Observation

Erythroid cells were cultured for maturation, treated with DiO cell membrane-labeling reagent for 5 min, and washed three times with buffer. After storage in a culture medium, the cells were cultured for 4 h and imaged using a live-cell imaging microscopy system whose environmental conditions were adjusted to those of an incubator for cell growth.

7. Biochemical Analysis

At days 19 and 21, culture media were collected, and glucose concentrations were determined using an automatic chemical analyzer. The pH and potassium ion ($K^+$) concentrations were analyzed using RapidSystems blood gas analyzers (Siemens, Medfield, Mass.). Lactate levels were measured using an enzymatic method with a Cobas Integra 800 (Roche Diagnostics, Rotkreuz, Switzerland).

8. RT-PCR

Total RNA was isolated using Trizol (Invitrogen) and was reverse-transcribed using SuperScript III Reverse Transcriptase (Invitrogen). Then, RT-PCR (LightCycler 480 II; Roche Diagnostics) was performed in triplicate using SYBR Premix ExTaq (Takara-Bio, Shiga, Japan). The relative quantitative analysis was normalized to endogenous β-actin. Primer sets designed using the Primer3 software were used and the primers were characterized by BLAST analysis.

The primer sequences were as follows (forward/reverse):

```
E-cadherin:
                                        (SEQ ID NO. 4)
5'-CGGGAATGCAGTTGAGGATC-3'
                                        (SEQ ID NO. 5)
5'-AGGATGGTGTAAGCGATGGC-3';

VLA-4:
                                        (SEQ ID NO. 6)
5'-AGGATGGTGTAAGCGATGGC-3'
                                        (SEQ ID NO. 7)
5'-TGCTGAAGAATTGGCTGAAGTGGTGG-3';

DLC-1:
                                        (SEQ ID NO. 8)
5'-AGTGCGTGCAACAAGCGGGT-3'
                                        (SEQ ID NO. 9)
5'-TCCGGGTAGCTCTCGCGGTT-3';

ICAM-4:
                                        (SEQ ID NO. 10)
5'-CCGGACTAAGCGGGCGCAAA-3'
                                        (SEQ ID NO. 11)
5'-AGCCACGAACTCCGGGCTCA-3'.
```

9. ELISA (Enzyme-Linked ImmunoSpecific Assay)

A primary antibody (ICAM-4, Santa Cruz, USA) was added to immuno-coated 96 well plates and allowed to stand at 4° C. for 20 h. Thereafter, the plates were washed three times with wash buffer (0.05% Tween-20 in PBS), and then 10% FBS in PBS was added thereto. After incubation for 2 h, the plates were washed three times with wash buffer. Supernatants collected after culture of the same number of cells were added to the plates, left standing at 4° C. for 18 h, and washed five times with wash buffer. An HRP-conjugated secondary antibody (Jackson ImmunoResearch Antibody, USA) was added and allowed to stand at room temperature. After incubation for 1 h, the plates were washed seven times with wash buffer and a detection solution (Biolegend. USA) was added for 30 min. The plates were read using an ELISA reader (Applied Biosystems, USA).

10. Western Blot

Total proteins were isolated using a lysis solution and 50 µg of the lysate was quantified before use. Thereafter, the lysate was electrophoresed on SDS-PAGE and transferred to a Hybond-ELC nitrocellulose membrane. The protein-transferred membrane was allowed to stand in 5% skin milk (in TBST: Tris buffer saline with Tween; 25 mM Tris, 140 mM NaCl, 0.05% Tween-20, pH 8.0) at room temperature for 1 h. Then, a primary antibody (DLC-1, Santa Cruz, USA) was added at 4° C. and stored for at least 12 h. The membrane was washed three times with TBST (each 10 min), and an HRP-conjugated secondary antibody (anti-rabbit, Jackson ImmunoResearch Antibody, USA) was added thereto. After standing at room temperature for 1 h, the membrane was washed three times with TBST (each 10 min). After addition of a detection reagent (ECL solution), the membrane was exposed to an X-ray film to identify the expression of the respective proteins.

11. Recombinant Protein Treatment

Erythroblasts in the stages of maturation were cultured on coated 24-well plates. After 2 h of culture, the purified recombinant ICAM-4 protein (OriGene Technologies, Baltimore, Md.) was added to the culture media at concentrations of 0, 2, 5, and 10 µg/ml and cultured for 24 h. After 24 h and 48 h of culture, the cells were stained, and their number and viability were measured and analyzed. The level of dysplasia, which is defined as the abnormal presence of 2-5 nuclei in one cell, enucleation rate, and the yield of red blood cells were measured and analyzed through cell imaging.

12. Statistical Analysis

Statistical analysis was conducted using the prism software (Prism, Version 5.0, GraphPad, San Diego, Calif.). Results are expressed as mean±standard deviation. p-values of less than 0.05 were considered significant. Paired t-tests were used to compare the sample groups.

Example 2: Test Results on Expanded Erythroid Cells (1) Effects of Interactions Between Homogenous Erythroid Cells Erythrocytes were produced from CD34+ cells in test tubes under serum-free and plasma-free conditions. CD34+ cells were cultured in erythroid differentiation media supplemented with EPO, IL-3, and SCF. From day 17 of culture when most of the cells were in the late stages of maturation (polychromatic (polychromatophilic) and orthochromatic erythroblasts), the cells were cultured at various densities (FIG. 1). As described in the previous study, the amount of the medium per well was maintained constant, whereas the number of cells per area varied between the wells.

Figure 2:
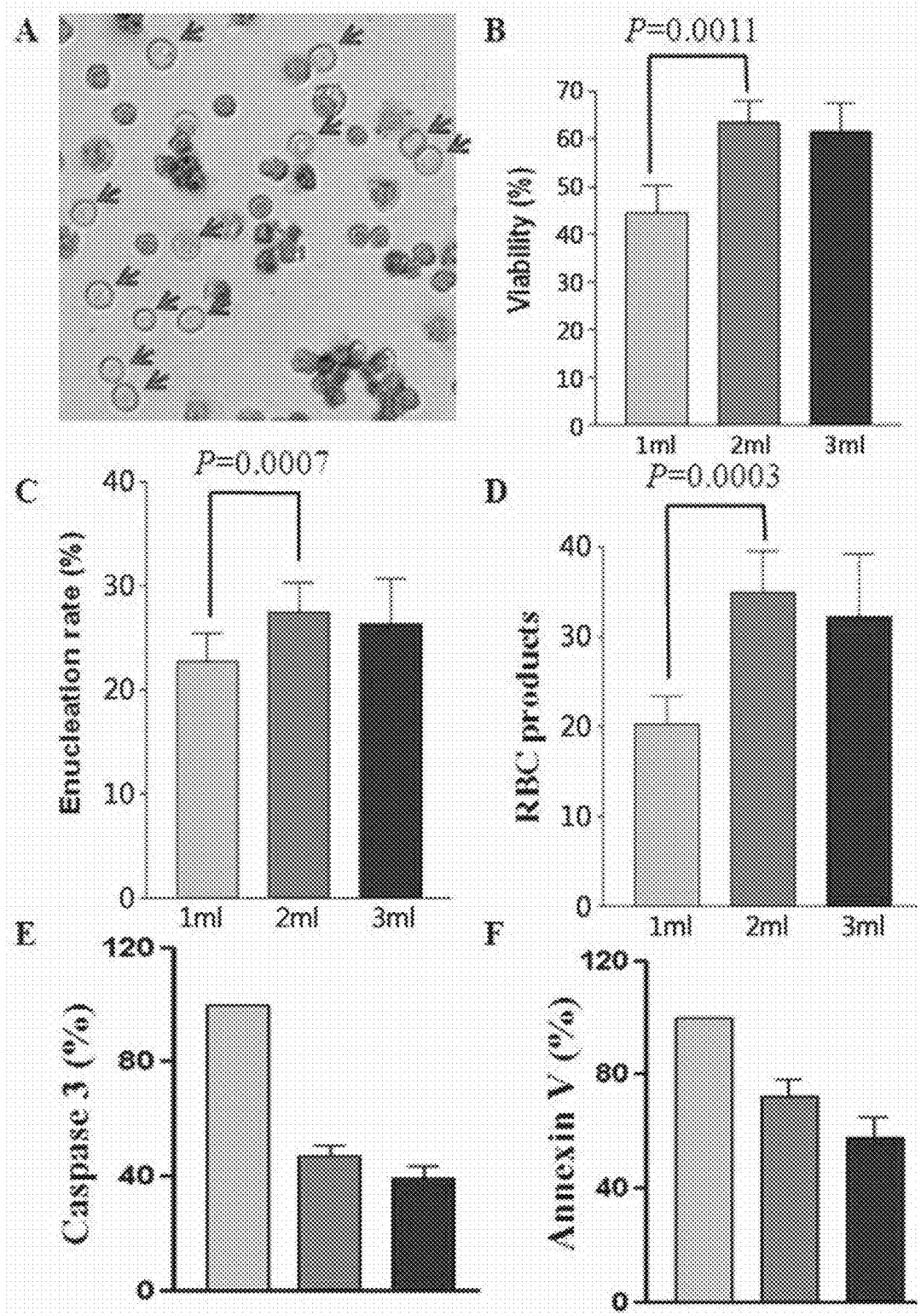
FIG. 2 shows the results of staining, enucleation rates, and apoptosis of erythroid cells cultured at 50%, 100%, and 150% confluences (Arrows indicate reticulocytes).

The effects of cell culture density on cell morphology during terminal maturation were evaluated using Wright-Giemsa staining. As a result of the cell staining, the morphology of the cells cultured at a lower density was not good (50% confluence; FIG. 2A), which was in good agreement with the result of viability obtained using trypan blue staining (FIG. 2B). In contrast, cells cultured at 100% and 150% confluences showed a significantly increased viability.

When erythroid cells exited the polychromatic (polychromatophilic) stage, cell proliferation declined and the rate of cell death markedly increased. Compared to the erythroid cells at 50% confluence (18.4%) ($p<0.05$) (FIG. 2C), high levels of enucleation were observed in the cells cultured at 100% and 150% confluences (25.5% and 20.6%, respectively).

When the enucleation rates at the corresponding cell densities were expressed as fold-expansion compared to the number of RBC products, the 50% confluence culture showed a significantly different profile from the 100% and 150% confluence cultures (paired t-tests, p<0.05) (FIG. 2D). At the 100% confluence, $8.6 \times 10^5$ reticulocytes were obtained with an enucleation rate of up to 40%.

At the stage of terminal erythroid maturation, the rate of apoptotic cell death markedly increased. Apoptosis analysis using Caspase-3 activation and Annexin V revealed that the apoptosis of cells cultured at 50% confluence was significantly low compared to that of cells cultured at 100% and 150% confluences (FIGS. 2E and 2F).

This increase in cell viability demonstrated that the highest expansion rate was obtained at 100% confluence. These results indicate that an increased cell density, i.e. a high cell density, can increase the chances of cell-to-cell contact to prevent apoptosis.

(2) Cell Maturation Analysis Through Morphology Evaluation and Flow Cytometry

Maturation from basophilic erythroblasts to polychromatophilic erythroblasts and/or orthochromatic erythroblasts was confirmed using Wright-Giemsa staining (data not shown).

Figure 3:
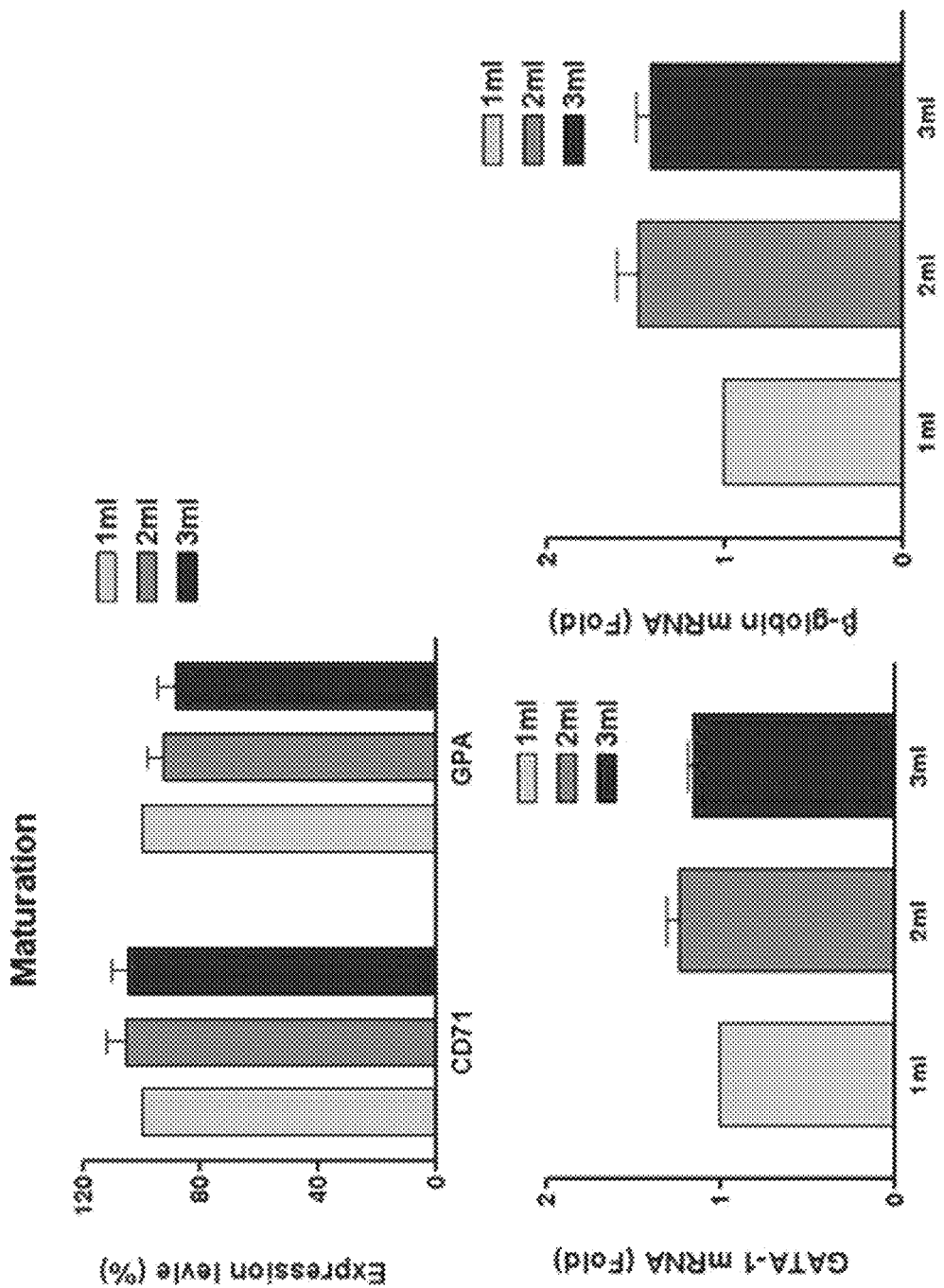
FIG. 3 shows the results of flow cytometry and RT-PCR for erythroid cells cultured at 50%, 100%, and 150% confluences in the terminal maturation stage.

On day 17 from the start of density experiments, flow cytometry was used to confirm the expression levels of CD71 (>53.7%) and GPA (>87.3%) corresponding to polychromatic (polychromatophilic) and orthochromatic stages, respectively (FIG. 3).

On day 21, the final day of density experiments, flow cytometry was used to measure changes in phenotype. As a result, the expression levels of CD71 and GPA did not differ significantly and those of maturation markers GATA-1 and Hbβ also did not differ markedly despite the different culture densities.

That is, the levels of erythroid maturation were similar at the three culture densities (FIG. 3).

(3) Analysis of Culture Media

To minimize the potential effects of metabolic regulation, culture densities were maintained constant. Glucose consumption, pH, and dissolved ion concentration were analyzed to evaluate culture conditions.

Figure 4:
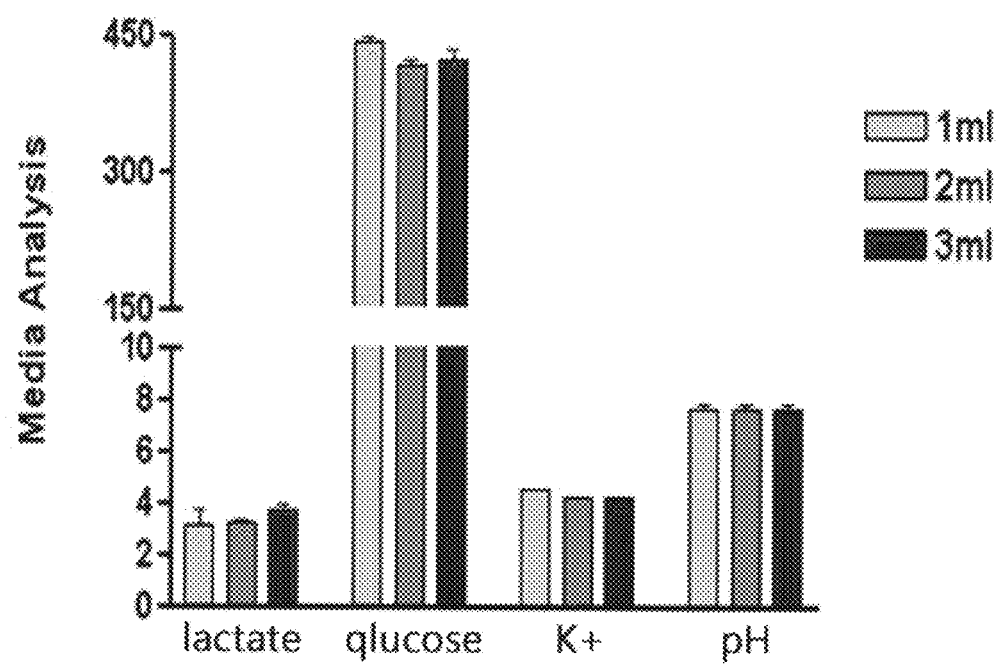
FIG. 4 shows the results of biochemical analysis for media used.

The average glucose consumption did not differ significantly between the low- and high-density cultures over the entire culture period (until day 21). The pH values and potassium concentrations of the media were similar under all density conditions (FIG. 4).

(4) Identification of Physical Binding Between Cells During Culture

Figure 5:
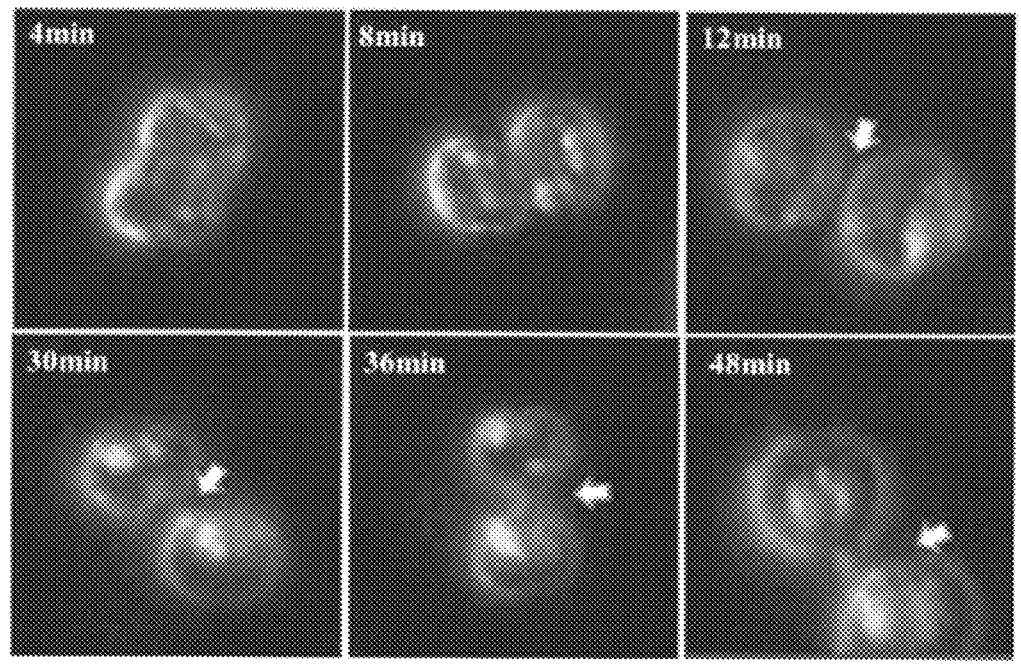
FIG. 5 shows erythroid cell contacts observed during erythropoiesis.

After staining of cell membranes with a dye reagent, the cell morphology was observed to determine physical binding between the cells. Binding of the cells was found to be different from cell division. As a result of analysis of the cell morphology, physical binding between the erythroid progenitor cells was demonstrated for the first time (FIG. 5).

(5) Contact-Related Changes in Gene Expression

To investigate the role of adhesion molecules in the terminal erythroid maturation, microarray analysis was used to find which genes were expressed differently during differentiation. The candidate genes included ICAM-4, VLA-4, DLC-1 and E-cadherin. The expression level of each gene in cells cultured at different densities was evaluated.

Figure 6:
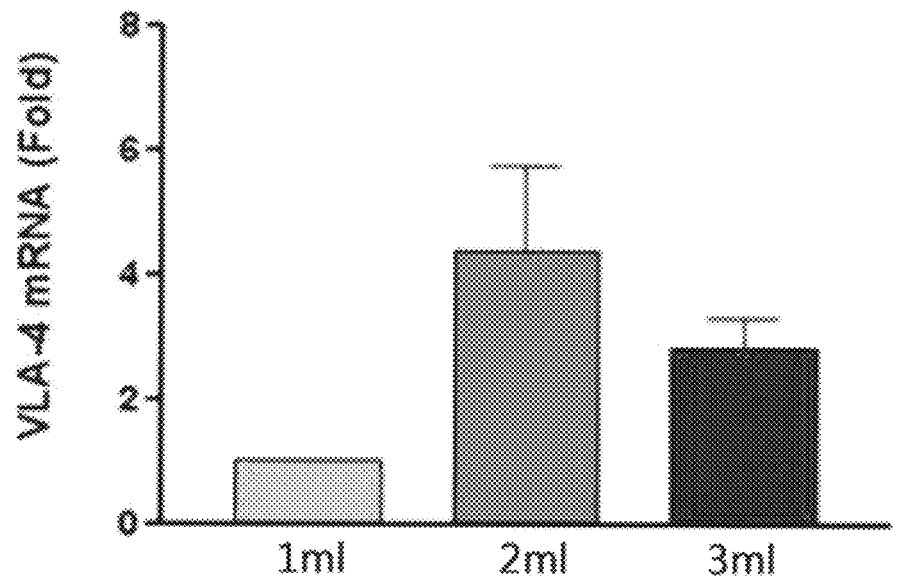
FIG. 6 shows the expression profiles of adhesion-related genes DLC-1 and VLA-4 at the terminal maturation stage of erythroid cells cultured at high densities.
Figure 6:
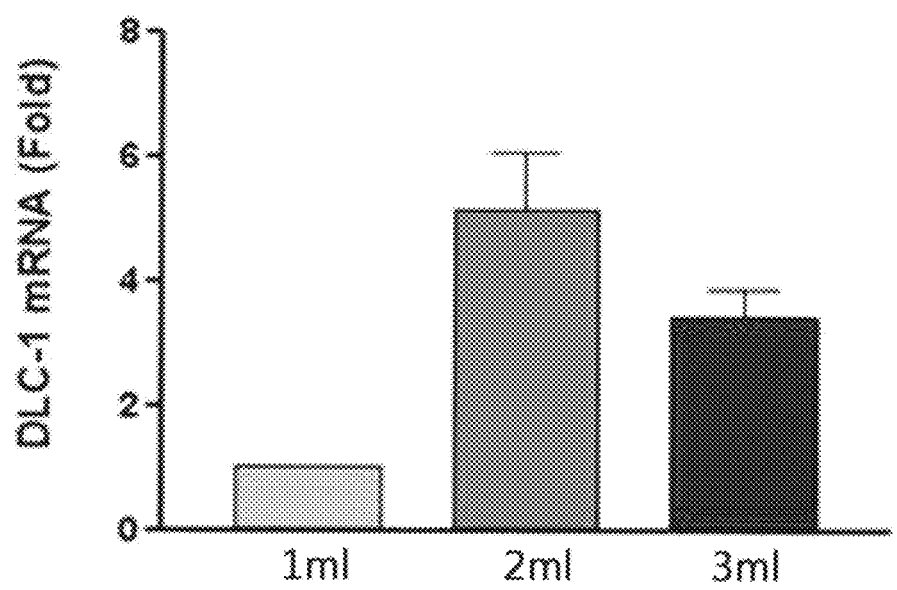

As shown in FIG. 6, both adhesion-related signaling genes VLA-4 and DLC-1 were overexpressed at medium and high levels of densities (100% and 150% confluences) (4.4- and 2.8-fold for VLA-4; 5.1- and 3.4-fold for DLC-1). The expression levels of the two genes were higher slightly at the 100% confluence.

As can be seen from these results, physical contact between erythroid cells induces autonomous adhesion-related signals by the expression of the adhesion-related signaling genes. That is, the erythroid cells cultured at high density secrete soluble signal factors, affecting the terminal cell maturation.

Figure 7:
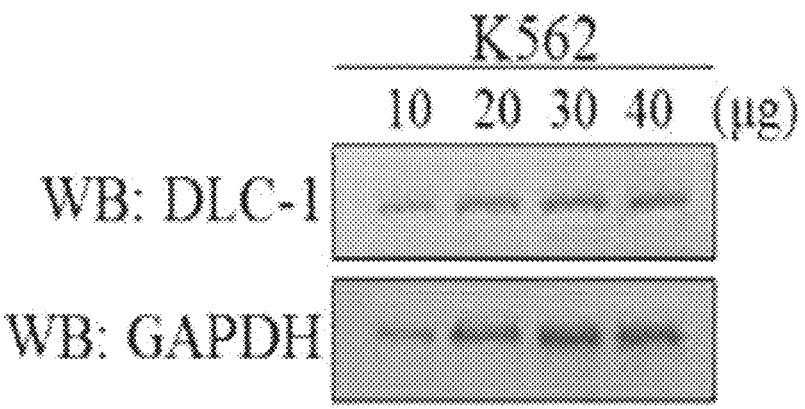
FIG. 7 shows the expression of DLC-1 in K562 cells.

(6) Expression Profiles of ICAM-4 and DLC-1 and Labeling Function on Erythroid Differentiation The present inventors discovered for the first time that DLC-1 expression was observed in K562 cells that can induce erythroid differentiation (FIG. 7). That is, the present inventors confirmed the expression of DLC-1 in erythroid cells.

The present inventors also discovered for the first time that the expression of DLC-1 and a secretory form of ICAM-4 in K562 cells, a cell line that can induce differentiation into erythrocytes.

Figure 8:
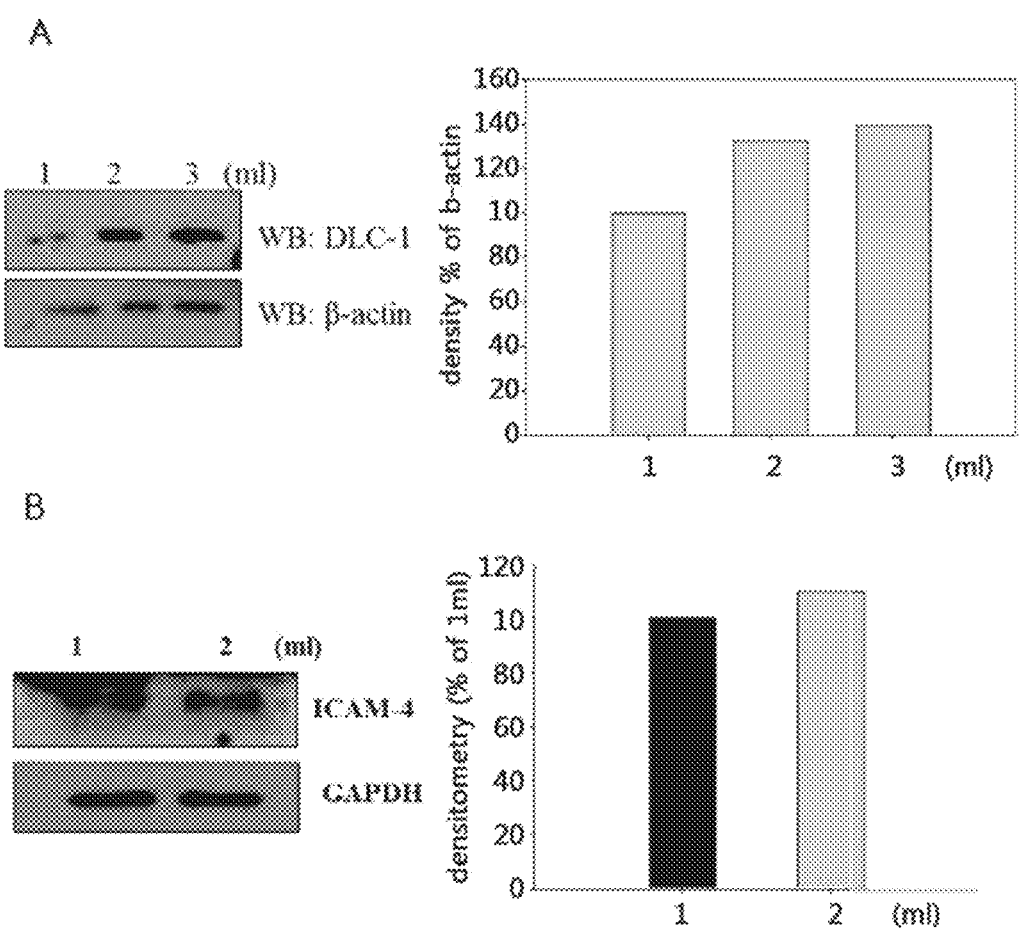
FIG. 8 shows the protein profiles of adhesion-related genes DLC-1 and ICAM-4 at the terminal maturation stage of erythroid cells cultured at high density.

The present inventors discovered through microarray analysis that the DLC-1 expression increases along with the maturation of erythroid cells. Particularly, the expression of DLC-1 was confirmed to affect density. It was confirmed that the expression of DLC-1 increases with increasing density and the resulting increased density is accompanied by an increase in enucleation rate (FIG. 8A).

Changes were also confirmed in ICAM-4 protein, which is already known to be expressed in erythroid cells and was confirmed through mRNA. ICAM-4 was confirmed to be expressed with increasing density, like mRNA (FIG. 8B).

The expression levels of DLC-1 and ICAM-4 increased with increasing density, resulting in an increased enucleation rate in medium- and high-density cultures.

In view of the foregoing, the present inventors confirmed binding of the two genes to demonstrate a relationship between the two genes.

Figure 9:
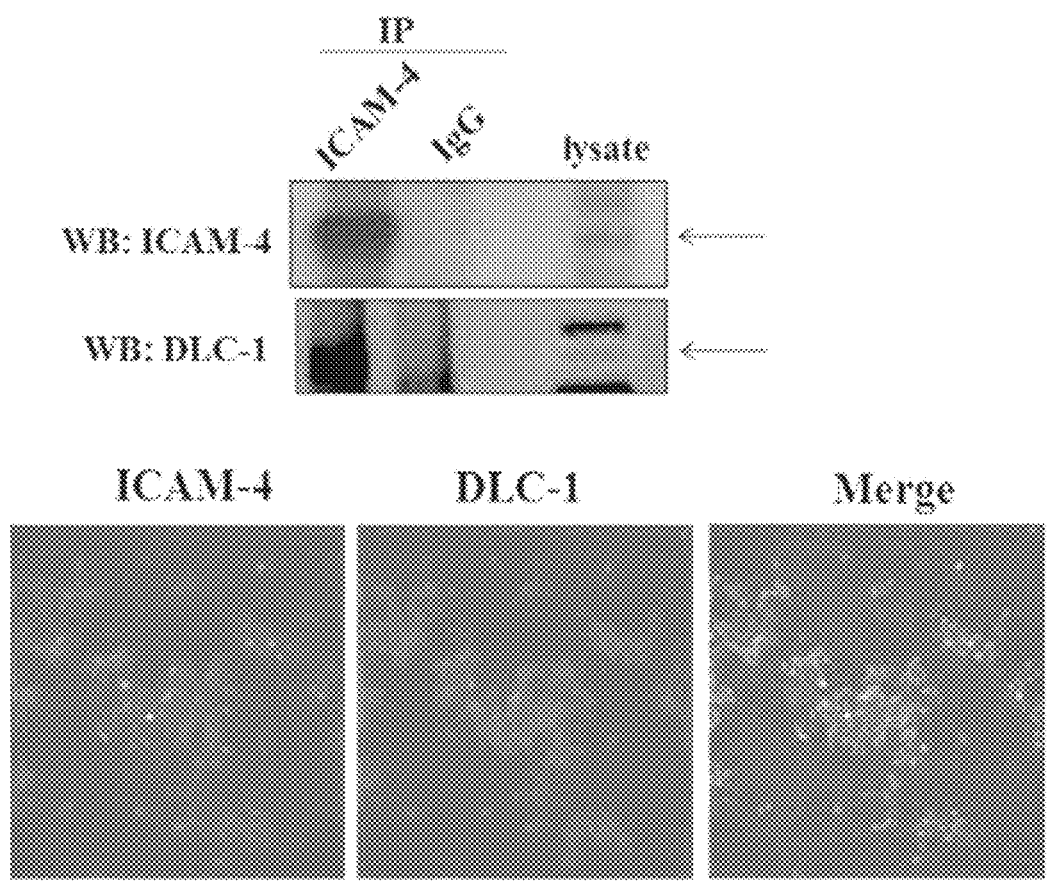
FIG. 9 shows binding between DLC-1 and ICAM-4 in K562 cells and fluorescence microscopy images showing similar expressions at expression sites of DLC-1 and ICAM-4 in human erythroid cells.

This is shown in FIG. 9. That is, the relationship between ICAM-4 and DLC-1 genes was confirmed through binding of proteins produced by the genes present in K562 cells. The optical microscopy images of FIG. 9 show the expression of DLC-1 in human erythroid cells and similar expressions of DLC-1 and ICAM-4 at expression sites thereof.

These results show that the binding of the two genes anticipated to play an important role in intercellular signal exchange will be associated with the contact of the two genes with the cells.

From this, it is anticipated that DLC-1 and ICAM-4 can be expressed in erythroid cells and will play a role in intercellular signal exchange. It has been shown that DLC-1, which has been reported to be found only in cancer cells, is associated with contact among cells, particularly, erythroid cells closely related to blood.

Therefore, the above experimental results suggest that DLC-1 and ICAM-4 can function as differentiation-specific markers in erythroid cells.

(7) Expression Profile of Secretory Form of ICAM-4

The expression of a secretory form of ICAM-4 was confirmed.

There was no report about the presence of a secretory form of ICAM-4 in mature erythrocytes. In the present invention, a determination was made as to whether or not and what extent ICAM-4 was expressed in K562 and mature erythrocytes.

Figure 10:
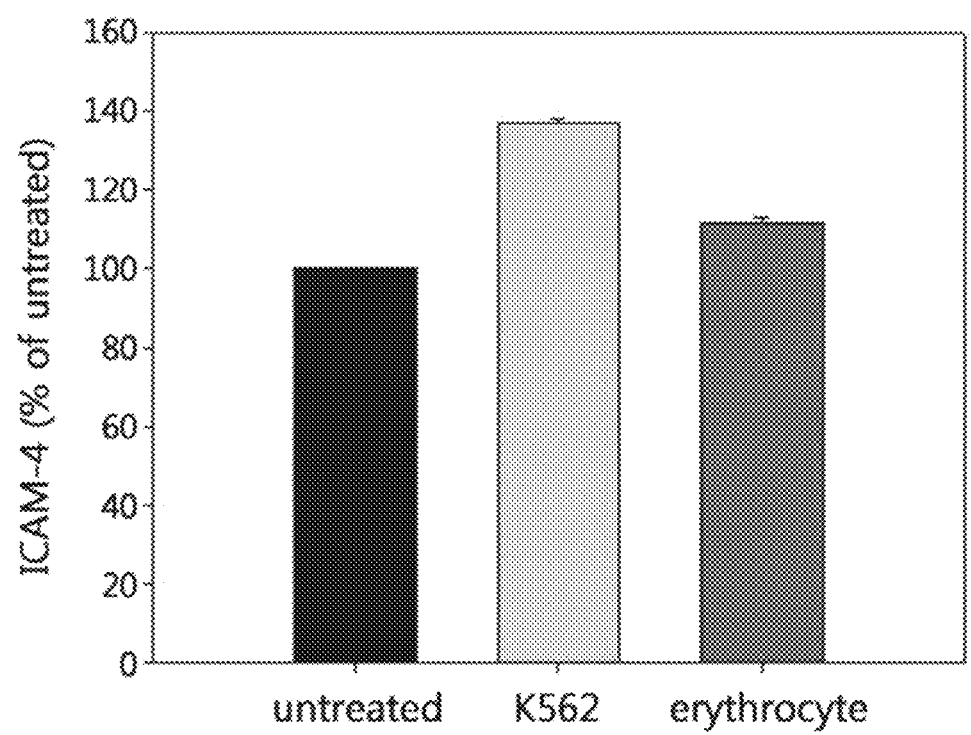
FIG. 10 shows the expression profiles of a secretory form of ICAM-4 secreted from cells and present in media.

As a result, when the expression level of the secretory form of ICAM-4 in untreated control (cell-free control media) was defined as 100%, the expression level of the secretory form of ICAM-4 was confirmed to be about 10% in the mature erythrocytes and about 40% in K562 cells, as shown in FIG. 10.

These results suggest that erythroid cell differentiation (erythropoiesis) is controlled by binding between cell membranes through direct binding of cells, as already known in the art, and soluble (water soluble) proteins, such as a secretory form of ICAM-4, play a direct or indirect role in cell differentiation.

(8) Enhancement of Terminal Maturation by ICAM-4

ICAM-4 was reported to be expressed only in erythroid cells. The present inventors intended to identify what role recombinant ICAM-4 plays in cells.

When erythroid cells in the stages of maturation were cultured after treatment with recombinant ICAM-4 at different concentrations (2, 5, and 10 μg/ul), the viability and enucleation rate of the cells were observed.

Figure 11:
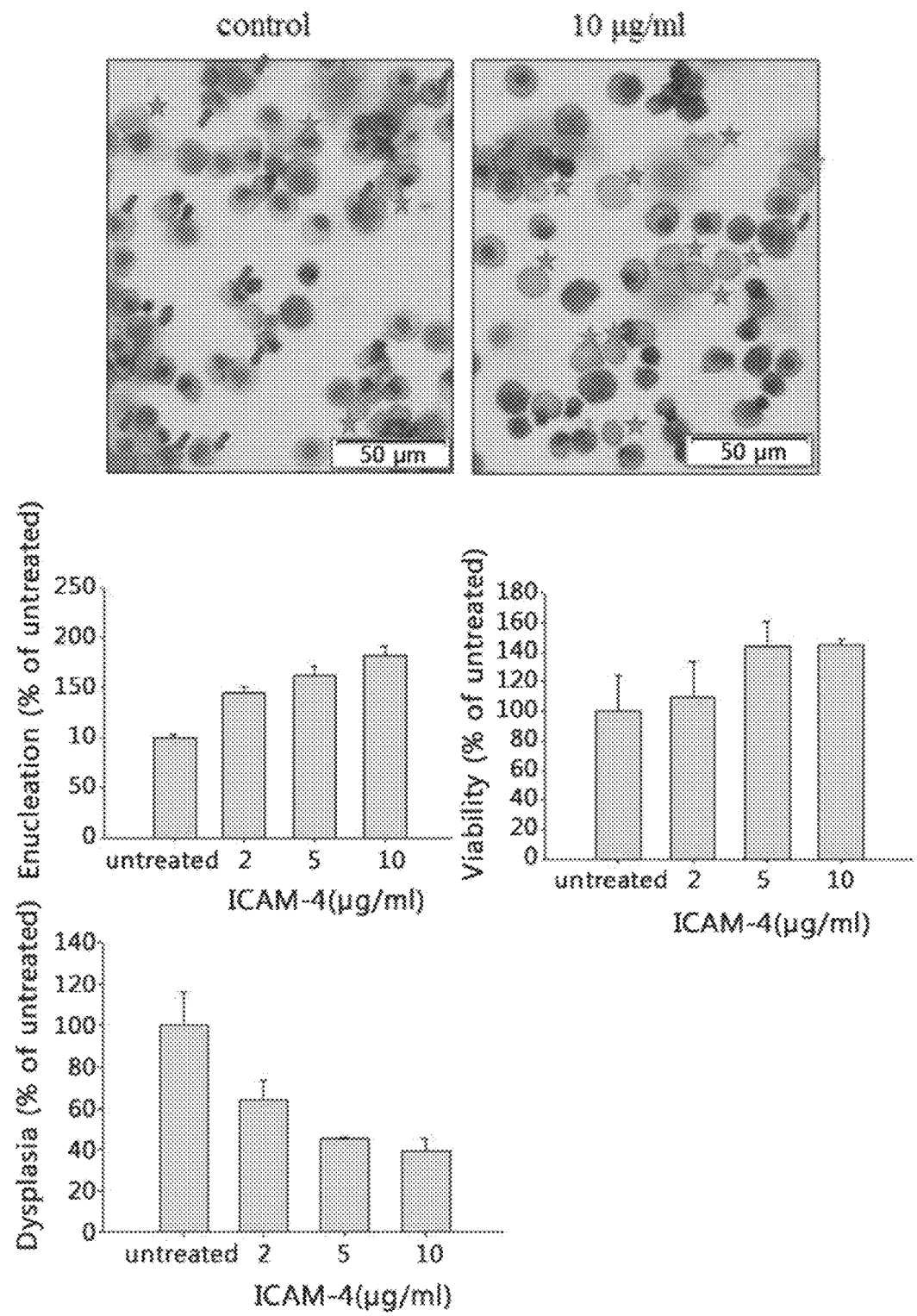
FIG. 11 shows the degrees of differentiation, viability rates, enucleation rates, degrees of dysplasia, and erythrocyte yields of late mature erythroblasts after the cells were treated with recombinant ICAM-4 protein.

FIG. 11 shows the degrees of differentiation, viability rates, enucleation rates, degrees of dysplasia, and erythrocyte yields of late mature erythroblasts after the cells were treated with recombinant ICAM-4 protein.

As can be seen from FIG. 11, as the concentration of the recombinant ICAM-4 increased, the intracellular dysplasia decreased and the enucleation rate increased, bringing about an increase in the productivity of erythrocytes. The number of the cells matured to erythrocytes was counted. As a result, it was shown that maturation was rapidly induced in proportion to the amount of the recombinant ICAM-4. These results indicate that ICAM-4 plays a role in promoting the production of erythrocytes from erythroid cells.

Example 3: 3D Culture

The production of erythrocytes during 3D culture using EP tubes simultaneously with the 24-well culture was observed.

An observation was made as to whether erythroid cells could be cultured even on a packed state in which intercellular contact was most maximized and whether cell viability decreased or cell aggregation occurred during culture.

On days 17-20 of culture, the culture of the erythroid cells in the form of a monolayer on the media described above and the culture of the erythroid cells on the packed state in the EP tubes were compared to determine whether the cells coagulated or their viability was lowered by compression. Live cells were counted weekly and cell morphology was observed under phase contrast microscopy.

Figure 12:
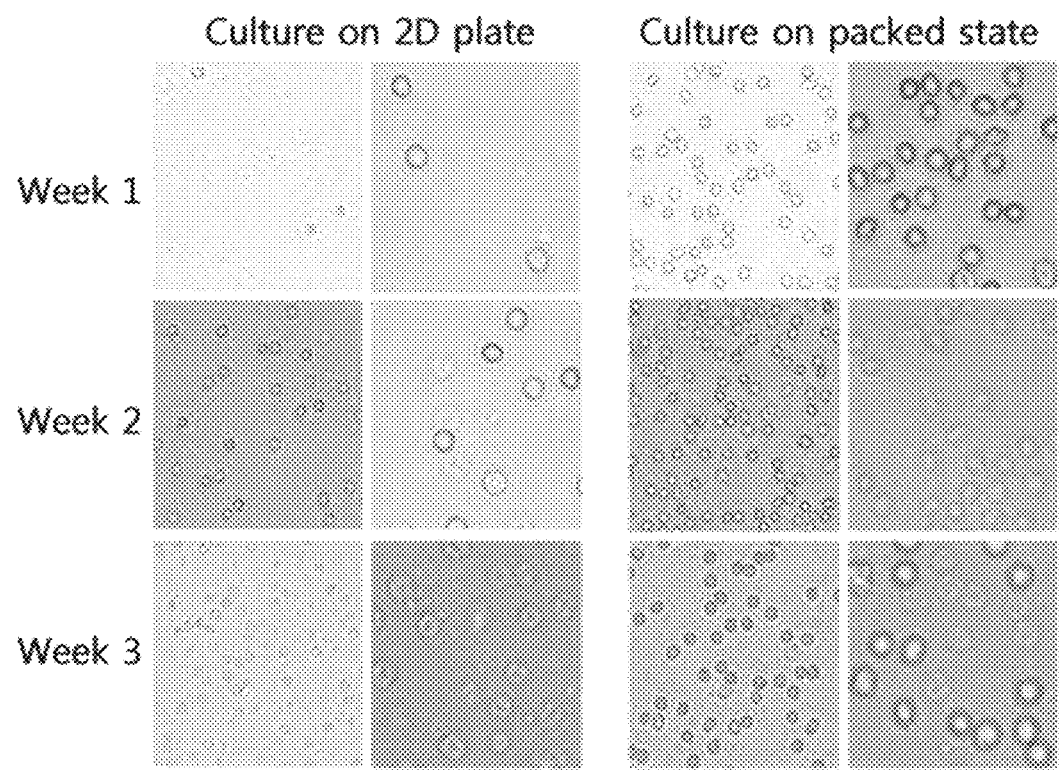
FIG. 12 shows the possibility of erythroid cell culture on a packed state and the morphologies of cells observed with phase contrast microscopy, in which the numbers of the cells were counted by trypan blue staining to determine the viability rates of the cells.
Figure 12:
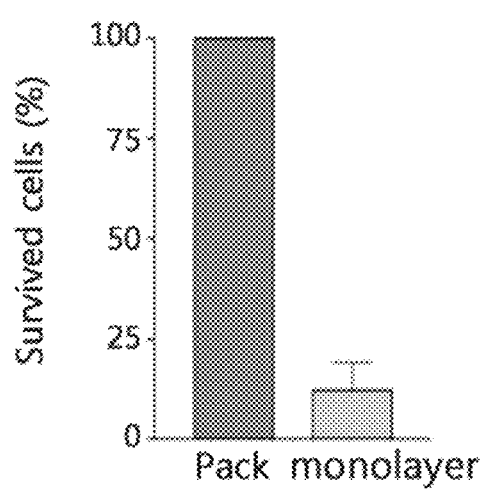

The results are shown in FIG. 12. Much higher viability (survival) under the packed conditions was found at week 2 of culture. That is, the culture method in which contact between the erythroid cells was maximized based on 3D culture was confirmed to be applicable to mass production of red blood cells.

The invention claimed is:

1. A method for in vitro expansion of erythroid cells, including culturing erythroid cells at a high density such that the cells come into direct physical contact with each other or in the presence of ICAM-4 protein,
   wherein the high density culture is performed at 100-150% confluence, wherein the 100% confluence is cell seeding and culturing at a density of about $5.0 \times 10^6$ cells/2 cm$^2$ and the 150% confluence is cell seeding and culturing at a density of about $7.5 \times 10^6$ cells/2 cm$^2$,
   wherein the culture in the presence of ICAM-4 protein is performed by the introduction of an ICAM-4 expression vector or the addition of ICAM-4 protein.

2. The method according to claim 1, wherein the erythroid cells are those that exit the terminal maturation stage.

3. The method according to claim 1, wherein the erythroid cells in direct physical contact with each other express at least one gene selected from adhesion-related genes DLC-1, ICAM-4, and VLA-4.

4. The method according to claim 3, wherein the signal exchange between the cells is activated by the expression of the gene to increase the productivity of red blood cells.

5. The method according to claim 3, wherein the binding and signal transduction between the erythroid cells are stimulated via ICAM-4 protein to be expressed.

6. The method according to claim 1, further comprising adding DLC-1 or VLA-4 protein to a culture medium of the erythroid cells.

7. The method according to claim 1, wherein the erythroid cells are cultured in a 2D or 3D configuration.

8. The method according to claim 7, wherein the erythroid cells are cultured in a 3D configuration in a state in which the erythroid cells are allowed to settle and packed.

9. A method for increasing the maturation of erythroid cells, comprising promoting the expression or activity of DLC-1, VLA-4, and ICAM-4, wherein the expression or activity of DLC-1, VLA-4 and ICAM-4 is promoted by the introduction of DLC-1, VLA-4, and ICAM-4 genes into the erythroid cells.

10. The method according to claim 9, wherein the maturation of the erythroid cells comprises enucleation.

11. A method for in vitro expansion of erythroid cells, comprising the method for increasing the maturation of erythroid cells according to claim 9.

\* \* \* \* \*

SEQUENCE LISTING

```
<160> NUMBER OF SEQ ID NOS: 11

<210> SEQ ID NO 1
<211> LENGTH: 3850
<212> TYPE: DNA
<213> ORGANISM: Homo sapiens

<400> SEQUENCE: 1
tatgggctcg agcggccgcc cgggcaggtg cccgagcgag ggcgcttcgc tcccagccag      60
gacatggccg cacctctccg catcaggagc gccggctcac ggacttctcg cccaactccc     120
tgagcgctcc ctcgtttcga tctttagaaa accccgcttt ctttctgggg ccgtgacgag     180
gggcagggag cggcgagcaa ggatgcgttg aggaccgcga gggcgcgcgt ctcgggtgcc     240
gccgtgggtc ccgacgcgga agccgagccg cctccgcctg cctcgacttc cccacagcgc     300
ttccgccgcc gcctgccgtg cttgatgtgc agaaagaagc cggacaccat gatcctaaca     360
caaattgaag ccaaggaagc ttgtgattgg ctacgggcaa ctggtttccc ccagtatgca     420
cagctttatg aagatttcct gttccccatc gatatttcct tggtcaagag agagcatgat     480
tttttggaca gagatgccat tgaggctcta tgcaggcgtc taaatacttt aaacaaatgt     540
gcggtgatga agctagaaat tagtcctcat cggaaacgaa gtgacgattc agacgaggat     600
gagccttgtg ccatcagtgg caaatggact ttccaaaggg acagcaagag gtggtcccgg     660
cttgaagagt ttgatgtctt ttctccaaaa caagacctgg tccctgggtc cccagacgac     720
tcccacccga aggacggccc cagccccgga ggcacgctga tggacctcag cgagcgccag     780
gaggtgtctt ccgtccgcag cctcagcagc actggcagcc tccccagcca cgcgcccccc     840
agcgaggatg ctgccacccc ccggactaac tccgtcatca gcgtttgctc ctccagcaac     900
ttggcaggca atgacgactc tttcggcagc ctgccctctc ccaaggaact gtccagcttc     960
agcttcagca tgaaaggcca cgaaaaaact gccagtcca agacgcgcag tctgctgaaa    1020
cggatggaga gcctgaagct caagagctcc catcacagca agcacaaagc gccctcaaag    1080
```

```
ctggggttga tcatcagcgg gcccatcttg caagagggga tggatgagga gaagctgaag    1140
cagctcagct gcgtggagat ctccgccctc aatggcaacc gcatcaacgt ccccatggta    1200
cgaaagagga gcgttccaa ctccacgcag accagcagca gcagcagcca gtcggagacc     1260
agcagcgcgg tcagcacgcc cagccctgtt acgaggaccc ggagcctcag tgcgtgcaac    1320
aagcgggtgg gcatgtactt agagggcttc gatcctttca atcagtcaac atttaacaac    1380
gtggtggagc agaactttaa gaaccgcgag agctacccag aggacacggt gttctacatc    1440
cctgaagatc acaagcctgg cactttcccc aaagctctca ccaatggcag tttctccccc    1500
tcggggaata acgctctgt gaactggagg acgggaagct tccacggccc tggccacatc     1560
agcctcagga gggaaaacag tagcgacagc cccaaggaac tgaagagacg caattcttcc    1620
agctccatga gcaccgcct gagcatctac gacaacgtgc cgggctccat cctctactcc     1680
agttcagggg acctggcgga tctggagaac gaggacatct cccccgagct ggacgacatc    1740
ctctaccacg tgaaggggat gcagcggata gtcaatcagt ggtcgagaa gttttctgat     1800
gagggagatt cggactcagc cctggactcg gtctctccct gcccgtcctc tccaaaacag    1860
atacacctgg atgtggacaa cgaccgaacc acacccagcg acctggacag cacaggcaac    1920
tccctgaatg aaccggaaga gccctccgag atcccggaaa aagggattc tggggttggg    1980
gcttccctaa ccaggtccaa caggcaccga ctgagatggc acagtttcca gagctcacat    2040
cggccaagcc tcaactctgt atcactacag attaactgcc agtctgtggc ccagatgaac    2100
ctgctgcaga atactccact cctaaagcta acggccctgc tggagaaata cacaccttct    2160
aacaagcatg gttttagctg gccgtgccc aagttcatga gaggatcaa ggttccagac     2220
tacaaggacc ggagtgtgtt tggggtccca ctgacggtca acgtgcagcg cacaggacaa    2280
ccgttgcctc agagcatcca gcaggccatg cgatacctcc ggaaccattg tttggatcag    2340
gttgggctct tcaaaaaatc gggggtcaag tcccggattc aggctctgcg ccagatgaat    2400
gaaggtgcca tagactgtgt caactacgaa ggacagtctg cttatgacgt ggcagacatg    2460
ctgaagcagt attttcgaga tcttcctgag ccactaatga cgaacaaact ctcggaaacc    2520
tttctacaga tctaccaata tgtgcccaag gaccagcgcc tgcaggccat caaggctgcc    2580
atcatgctgc tgcctgacga gaaccggggtg gttctgcaga ccctgcttta tttcctgtgc    2640
gatgtcacag cagccgtaaa agaaaaccag atgacccca ccaacctggc cgtgtgctta     2700
gcgcctttccc tcttccatct caacacccctg aagagagaga attcctctcc cagggtaatg    2760
caaagaaaac aaagtttggg caaaccagat cagaaagatt tgaatgaaaa cctagctgcc    2820
actcaagggc tggcccatat gatcgccgag tgcaagaagc ttttccaggt tcccgaggaa    2880
atgagccgat gtcgtaattc ctataccgaa caagagctga gcccctcac tctggaagca    2940
ctcgggcacc tgggtaatga tgactcagct gactaccaac acttcctcca ggactgtgtg    3000
gatggcctgt ttaaagaagt caaagagaag tttaaaggct gggtcagcta ctccacttcg    3060
gagcaggctg agctgtccta taagaaggtg agcgaaggac cccgtctgag gctttggagg    3120
tcagtcattg aagtccctgc tgtgccagag gaaatcttaa agcgcctact taagaacag    3180
cacctctggg atgtagacct gttggattca aaagtgatcg aaattctgga cagccaaact    3240
gaaatttacc agtatgtcca aaacagtatg gcacctcatc ctgctcgaga ctacgttgtt    3300
ttaagaacct ggaggactaa tttacccaaa ggagcctgtg cccttttact aacctctgtg    3360
gatcacgatc gcgcacctgt ggtgggtgtg agggttaatg tgctcttgtc caggtatttg    3420
```

| | |
|---|---|
| attgaaccct gtgggccagg aaaatccaaa ctcacctaca tgtgcagagt tgacttaagg | 3480 |
| ggccacatgc cagaatggta cacaaaatct tttggacatt tgtgtgcagc tgaagttgta | 3540 |
| aagatccggg attccttcag taaccagaac actgaaacca agacaccaa atctaggtga | 3600 |
| tcactgaagc aacgcaaccg cttccaccac catggtgttt gttttagaa gttttgccag | 3660 |
| tccttgaaga atgggttctg tgtgtaatcc tgaaacaaag aaaactacaa gctggagtgt | 3720 |
| aggaattgac tatagcaatt tgatacattt ttaaagctgc ttcctgtttg ttgagggtct | 3780 |
| gtattcatag accttgactg aatatgtaa gactgtgcga aaaaaaaaa aaaaaaaaa | 3840 |
| aaaaaaaaaa | 3850 |

<210> SEQ ID NO 2
<211> LENGTH: 6082
<212> TYPE: DNA
<213> ORGANISM: Homo sapiens

<400> SEQUENCE: 2

| | |
|---|---|
| ataacgtctt tgtcactaaa atgttcccca ggggccttcg gcgagtcttt ttgtttggtt | 60 |
| ttttgttttt aatctgtggc tcttgataat ttatctagtg gttgcctaca cctgaaaaac | 120 |
| aagacacagt gtttaactat caacgaaaga actggacggc tccccgccgc agtcccactc | 180 |
| cccgagtttg tggctggcat ttgggccacg ccgggctggg cggtcacagc gaggggcgcg | 240 |
| cagtttgggg tcacacagct ccgcttctag gccccaacca ccgttaaaag gggaagcccg | 300 |
| tgccccatca ggtccgctct tgctgagccc agagccatcc cgcgctctgc gggctgggag | 360 |
| gcccgggcca ggacgcgagt cctgcgcagc cgaggttccc cagcgccccc tgcagccgcg | 420 |
| cgtaggcaga gacggagccc ggccctgcgc ctccgcacca gcccgggac cccacccagc | 480 |
| ggcccgtacc cggagaagca gcgcgagcac ccgaagctcc cggctggcgg cagaaaccgg | 540 |
| gagtgggggcc gggcgagtgc gcggcatccc aggccggccc gaacgctccg cccgcggtgg | 600 |
| gccgacttcc cctcctcttc cctctctcct tcctttagcc cgctggcgcc ggacacgctg | 660 |
| cgcctcatct cttggggcgt tcttcccgt tggccaaccg tcgcatcccg tgcaactttg | 720 |
| gggtagtggc cgtttagtgt tgaatgttcc ccaccgagag cgcatggctt gggaagcgag | 780 |
| gcgcgaaccc ggcccccgaa gggccgccgt ccgggagacg gtgatgctgt tgctgtgcct | 840 |
| gggggtcccg accggccgcc cctacaacgt ggacactgag agcgcgctgc tttaccaggg | 900 |
| cccccacaac acgctgttcg gctactcggt cgtgctgcac agccacgggg cgaaccgatg | 960 |
| gctcctagtg ggtgcgccca ctgccaactg gctcgccaac gcttcagtga tcaatcccgg | 1020 |
| ggcgatttac agatgcagga tcggaaagaa tcccggccag acgtgcgaac agctccagct | 1080 |
| gggtagccct aatggagaac cttgtggaaa gacttgtttg gaagagagag acaatcagtg | 1140 |
| gttggggggtc acactttcca gacagccagg agaaaatgga tccatcgtga cttgtgggca | 1200 |
| tagatggaaa aatatatttt acataaagaa tgaaataag ctccccactg gtggttgcta | 1260 |
| tggagtgccc cctgatttac gaacagaact gagtaaaaga atagctccgt gttatcaaga | 1320 |
| ttatgtgaaa aaatttggag aaaattttgc atcatgtcaa gctggaatat ccagttttta | 1380 |
| cacaaaggat ttaattgtga tggggccccc aggatcatct tactgactg gctctctttt | 1440 |
| tgtctacaat ataactacaa ataaatacaa ggcttttta gacaaacaaa atcaagtaaa | 1500 |
| atttggaagt tatttaggat attcagtcgg agctggtcat tttcggagcc agcatactac | 1560 |
| cgaagtagtc ggaggagctc ctcaaactga gcagattggt aaggcatata tattcagcat | 1620 |
| tgatgaaaaa gaactaaata tcttacatga aatgaaaggt aaaagcttg gatcgtactt | 1680 |

```
tggagcttct gtctgtgctg tggacctcaa tgcagatggc ttctcagatc tgctcgtggg    1740
agcacccatg cagagcacca tcagagagga aggaagagtg tttgtgtaca tcaactctgg    1800
ctcgggagca gtaatgaatg caatggaaac aaacctcgtt ggaagtgaca aatatgctgc    1860
aagatttggg gaatctatag ttaatcttgg cgacattgac aatgatggct ttgaagatgt    1920
tgctatcgga gctccacaag aagatgactt gcaaggtgct atttatattt acaatggccg    1980
tgcagatggg atctcgtcaa ccttctcaca gagaattgaa ggacttcaga tcagcaaatc    2040
gttaagtatg tttggacagt ctatatcagg acaaattgat gcagataata atggctatgt    2100
agatgtagca gttggtgctt ttcggtctga ttctgctgtc ttgctaagga caagacctgt    2160
agtaattgtt gacgcttctt taagccaccc tgagtcagta aatagaacga aatttgactg    2220
tgttgaaaat ggatggcctt ctgtgtgcat agatctaaca ctttgtttct catataaggg    2280
caaggaagtt ccaggttaca ttgttttgtt ttataacatg agtttggatg tgaacagaaa    2340
ggcagagtct ccaccaagat tctatttctc ttcaatgga acttctgacg tgattacagg    2400
aagcatacag gtgtccagca gagaagctaa ctgtagaaca catcaagcat ttatgcggaa    2460
agatgtgcgg gacatcctca ccccaattca gattgaagct gcttaccacc ttggtcctca    2520
tgtcatcagt aaacgaagta cagaggaatt cccaccactt cagccaattc ttcagcagaa    2580
gaaagaaaaa gacataatga aaaaacaat aaactttgca aggttttgtg cccatgaaaa    2640
ttgttctgct gatttacagg tttctgcaaa gattgggttt ttgaagcccc atgaaaataa    2700
aacatatctt gctgttggga gtatgaagac attgatgttg aatgtgtcct tgtttaatgc    2760
tggagatgat gcatatgaaa cgactctaca tgtcaaacta cccgtgggtc tttatttcat    2820
taagatttta gagctggaag agaagcaaat aaactgtgaa gtcacagata actctggcgt    2880
ggtacaactt gactgcagta ttggctatat atatgtagat catctctcaa ggatagatat    2940
tagctttctc ctggatgtga gctcactcag cagagcggaa gaggacctca gtatcacagt    3000
gcatgctacc tgtgaaaatg aagaggaaat ggacaatcta aagcacagca gagtgactgt    3060 agcaataccct ttaaaatatg aggttaagct gactgttcat gggtttgtaa acccaacttc    3120
atttgtgtat ggatcaaatg atgaaaatga gcctgaaacg tgcatggtgg agaaaatgaa    3180
cttaactttc catgttatca acactggcaa tagtatggct cccaatgtta gtgtggaaat    3240
aatggtacca aattctttta gcccccaaac tgataagctg ttcaacattt tggatgtcca    3300
gactactact ggagaatgcc actttgaaaa ttatcaaaga gtgtgtgcat tagagcagca    3360
aaagagtgca atgcagacct tgaaaggcat agtccggttc ttgtccaaga ctgataagag    3420
gctattgtac tgcataaaag ctgatccaca ttgtttaaat ttcttgtgta attttgggaa    3480
aatggaaagt ggaaaagaag ccagtgttca tatccaactg gaaggccggc catccatttt    3540
agaaatggat gagacttcag cactcaagtt tgaaataaga gcaacaggtt ttccagagcc    3600
aaatccaaga gtaattgaac taaacaagga tgagaatgtt gcgcatgttc tactggaagg    3660
actacatcat caaagaccca acgttatttt caccatagtg attatttcaa gtagcttgct    3720
acttggactt attgtacttc tgttgatctc atatgttatg tggaaggctg gcttctttaa    3780
aagacaatac aaatctatcc tacaagaaga aaacagaaga gacagttgga gttatatcaa    3840
cagtaaaagc aatgatgatt aaggacttct ttcaaattga gagaatggaa aacagactca    3900
ggttgtagta agaaaatta aaagacactg tttacaagaa aaaatgaatt ttgtttggac    3960 ttctttttact catgatcttg tgacatatta tgtcttcatg caaggggaaa atctcagcaa    4020
```

| | |
|---|---|
| tgattactct ttgagataga agaactgcaa aggtaataat acagccaaag ataatctctc | 4080 |
| agcttttaaa tgggtagaga aacactaaag cattcaattt attcaagaaa agtaagccct | 4140 |
| tgaagatatc ttgaaatgaa agtataactg agttaaatta tactggagaa gtcttagact | 4200 |
| tgaaatacta cttaccatat gtgcttgcct cagtaaaatg aacccactg ggtgggcaga | 4260 |
| ggttcatttc aaatacatct ttgatacttg ttcaaaatat gttctttaaa aatataattt | 4320 |
| tttagagagc tgttcccaaa ttttctaacg agtggaccat tatcacttta aagcccttta | 4380 |
| tttataatac atttcctacg ggctgtgttc caacaaccat tttttttcag cagactatga | 4440 |
| atattatagt attataggcc aaactggcaa acttcagact gaacatgtac actggtttga | 4500 |
| gcttagtgaa attacttctg ataattatt tttttataat tatggatttc accatctttc | 4560 |
| tttctgtata tatacatgtg ttttttatgta ggtatatatt taccattctt cctatctatt | 4620 |
| cttcctataa cacacctttta tcaagcatac ccaggagtaa tcttcaaatc ttttgttata | 4680 |
| ttctgaaaca aaagattgtg agtgttgcac tttacctgat acacgctgat ttagaaaata | 4740 |
| cagaaaccat acctcactaa taactttaaa atcaaagctg tgcaaagact agggggccta | 4800 |
| tacttcatat gtattatgta ctatgtaaaa tattgactat cacacaacta tttccttgga | 4860 |
| tgtaattctt tgttaccctt tacaagtata agtgttacct tacatggaaa cgaagaaaca | 4920 |
| aaattcataa atttaaattc ataaatttag ctgaaagata ctgattcaat ttgtatacag | 4980 |
| tgaatataaa tgagacgaca gcaaaatttt catgaaatgt aaaatatttt tatagtttgt | 5040 |
| tcatactata tgaggttcta ttttaaatga cttctggat tttaaaaat ttctttaaat | 5100 |
| acaatcattt ttgtaatatt tatttatgc ttatgatcta gataattgca gaatatcatt | 5160 |
| ttatctgact ctgccttcat aagagagctg tggccgaatt ttgaacatct gttataggga | 5220 |
| gtgatcaaat tagaaggcaa tgtggaaaaa caattctggg aaagatttct ttatatgaag | 5280 |
| tccctgccac tagccagcca tcctaattga tgaaagttat ctgttcacag gcctgcagtg | 5340 |
| atggtgagga atgttctgag atttgcgaag gcatttgagt agtgaaatgt aagcacaaaa | 5400 |
| cctcctgaac ccagagtgtg tatacacagg aataaacttt atgacattta tgtatttta | 5460 |
| aaaaacttttg tatcgttata aaaggctag tcattctttc aggagaacat ctaggatcat | 5520 |
| agatgaaaaa tcaagccccg atttagaact gtcttctcca ggatggtctc taaggaaatt | 5580 |
| tacatttggt tctttcctac tcagaactac tcagaaacaa ctatatattt caggttatct | 5640 |
| gagcacagtg aaagcagagt actatggttg tccaacacag gcctctcaga tacaagggga | 5700 |
| acacaattac atattgggct agattttgcc cagttcaaaa tagtatttgt tatcaactta | 5760 |
| ctttgttact tgtatcatga atttaaaac cctaccactt taagaagaca gggatgggtt | 5820 |
| attctttttt ggcaggtagg ctatataact atgtgatttt gaaatttaac tgctctggat | 5880 |
| tagggagcag tgaatcaagg cagacttatg aaatctgtat tatatttgta acagaatata | 5940 |
| ggaaatttaa cataattgat gagctcaaat cctgaaaaat gaaagaatcc aaattatttc | 6000 |
| agaattatct aggttaaata ttgatgtatt atgatggttg caagttttt ttgtgtgtcc | 6060 |
| aataaacaca ttgtaaaaaa aa | 6082 |

<210> SEQ ID NO 3
<211> LENGTH: 3448
<212> TYPE: DNA
<213> ORGANISM: Homo sapiens

<400> SEQUENCE: 3

| | |
|---|---|
| cggggtctcg caacattgcc cagacttcct ttgtgttagt taataaagct ttctcaactg | 60 |

```
cctcagcctt gtgtgagttg aggggaggtg tcacatccag ctggagtcct ttctaagcag       120
ccacagcctg atcctcccac ttcctccccc aagaaaacat tgtgggttga tggccatacc      180
ctgaggttct ggtccaaatc ggactttcta tgaccttctg ggtctctagt gaaaactaaa      240
gactcctctc cagaaaaaaa catttggttt ctaatgaggc ctggaatctt attcttgacc      300
tggggagcgg aatccctttt tgcagtactc ccgggccctc tgttggggcc tccccttcct     360
ctccagggtg gagtcgagga ggcggggctg cgggcctcct tatctctaga gccggccctg     420
gctctctggc gcggggcccc ttagtccggg ctttttgcca tggggtctct gttccctctg     480
tcgctgctgt tttttttggc ggccgcctac ccgggagttg ggagcgcgct gggacgccgg     540
actaagcggg cgcaaagccc caagggtagc cctctcgcgc cctccgggac ctcagtgccc     600
ttctgggtgc gcatgagccc ggagttcgtg gctgtgcagc cggggaagtc agtgcagctc     660
aattgcagca acagctgtcc ccagccgcag aattccagcc tccgcacccc gctgcggcaa     720
ggcaagacgc tcagggggcc gggttgggtg tcttaccagc tgctcgacgt gagggcctgg     780
agctccctcg cgcactgcct cgtgacctgc gcaggaaaaa cacgctgggc cacctccagg     840
atcaccgcct acagtgaggg acaggggctc ggtcccggct ggggtgaggg gaggggggctg     900 gaagaggtgg gggaagggta gttgacagtc gctctatagg gagcgcccgc ggacctcact     960
cagaggctcc cccttgcctt agaaccgccc cacagcgtga ttttggagcc tccggtctta    1020
aagggcagga aatacacttt gcgctgccac gtgacgcagg tgttcccggt gggctacttg    1080
gtggtgaccc tgaggcatgg aagccgggtc atctattccg aaagcctgga gcgcttcacc    1140
ggcctggatc tggccaacgt gaccttgacc tacgagtttg ctgctggacc ccgcgacttc    1200
tggcagcccg tgatctgcca cgcgcgcctc aatctcgacg gcctggtggt ccgcaacagc    1260
tcggcaccca ttacactgat gctcggtgag gcacccctgt aaccctgggg actaggagga    1320 aggggggcaga gagagttatg accccgagag ggcgcacaga ccaagcgtga gctccacgcg   1380
ggtcgacaga cctccctgtg ttccgttcct aattctcgcc ttctgctccc agcttggagc    1440
cccgcgccca cagctttggc ctccggttcc atcgctgccc ttgtagggat cctcctcact    1500
gtgggcgctg cgtacctatg caagtgccta gctatgaagt cccaggcgta aagggggatg    1560
ttctatgccg gctgagcgag aaaaagagga atatgaaaca atctgggaa atggccatac    1620 atggtggctg acgcctgtaa tcccagcact ttgggaggcc gaggcaggag aatcgcttga    1680
gcccaggagt tcgagaccag cctggacaac atagtgagac ccgtctatg caaaaaatac     1740 acaaattagc ctggtgtggt ggccgcacc tgtggtccca gctacccggg aggctgagtt     1800
gggaggatcc tttgagcct gaaagtcgag gttgcagtga gccttgatcg tgccactgca    1860
ctccagcctg gggacagag cacgaccctg tctccaaaaa taaataaaa ataaaaataa      1920 atattggcgg gggaaccctc tggaatcaat aaaggcttcc ttaaccagcc tctgtcctgt    1980
gacctaaggg tccgcattac tgcccttctt cggaggaact ggtttgtttt tgttgttgtt    2040 gttgttttg cgatcacttt ctccaagttc cttgtctccc tgagggcacc tgaggtttcc    2100
tcactcaggg cccacctggg gtcccgaagc cccagactct gtgtatcccc agcgggtgtc    2160
acagaaacct ctccttctgc tggccttatc gagtgggatc agcgcgggcc ggggagagcc    2220
acgggcaggg gcggggtggg gttcatggta tggctttcct gattggcgcc gccgccacca    2280
cgcggcagct ctgattggat gttaagtttc ctatcccagc cccaccttca gaccctgtgc    2340
tttcctggag gccaaacaac tgtggagcga gaactcatct ccaaaataac ttaccacgct    2400
```

```
ggagtgagac cacgaatggt ggggagggga gggtcccacg acatattga gggacgtgga    2460 tacgcagaag aggtatccat gtggtggcag ccgggaaggg gtgatcagat ggtccacagg    2520
gaatatcaca aactcgaatt ctgacgatgt tctggtagtc acccagccag atgagcgcat    2580
ggagttgggg gtgggggtg tcaaagcttg gggcccggaa gcggagtcaa aagcatcacc     2640
ctcggtccct tgttctcgcg tggatgtcag ggcccccacc caccgagcag aaggcggact    2700
caggggcgct ccagggtggc tcgagctcac acacgctgag tagacacgtg cccgctgcac    2760
cctgggtaaa tacagacccg gagccgagcg gattctaatt tagacgcccg cgaacgctgc    2820
gcgcacgcac acgtgtcctc ggctcgctgg cactttcgtc ccgccccctc cgtcgcgtgc    2880
cggagctgac ccggaggggt gcttagaggt atggctccgc ggggtcaaaa ggagaaggat    2940
cagtgagaga ggcatcccca caccctcccc tagaactgtc cttccccat ccagtgcctc     3000 ccaaatctct cttagtcccc aaatgtatcc ccgccctaag gggcgctggt gggaggagct    3060
aaatgtgggg gcggagctcg gagtccagct tattatcatg gcatctcagc cagggctggg    3120
gtaggggttt gggaagggca acccagcatc ccccgatccc agagtcgcgg ccggggatga    3180
cgcgagagag cgtggtcgcc cccagaaggc cctgggccat catgccggcc tccacgtaga    3240 ccccagggt cgctcactcc tgccagctcg ccttcaccaa ggccaggagc ttagcgcacg     3300
ctcgcctccc gccccccgc cgcctctgcc gccgccccct ccttggaaac caagttacca     3360
acgttaaacc aatccccaag cgcaactctg cctcccccac accccacccg ccgcgccgcg    3420
cggagccgtc ctctagccca gctcctcg                                       3448

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer for E-cadherin

<400> SEQUENCE: 4
cgggaatgca gttgaggatc                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer for E-cadherin

<400> SEQUENCE: 5
aggatggtgt aagcgatggc                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer for VLA-4

<400> SEQUENCE: 6
aggatggtgt aagcgatggc                                                  20

<210> SEQ ID NO 7
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      reverse primer for VLA-4

<400> SEQUENCE: 7
tgctgaagaa ttggctgaag tggtgg                                             26

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer for DLC-1

<400> SEQUENCE: 8
agtgcgtgca acaagcgggt                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer for DLC-1

<400> SEQUENCE: 9
tccgggtagc tctcgcggtt                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer for ICAM-4

<400> SEQUENCE: 10
ccggactaag cgggcgcaaa                                                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer for ICAM-4

<400> SEQUENCE: 11
agccacgaac tccgggctca                                                    20
```